United States Patent
Benitez et al.

(10) Patent No.: US 11,660,015 B2
(45) Date of Patent: May 30, 2023

(54) IMAGING COMPATIBLE FOOT STRESSOR FOR USE IN DIAGNOSING FOOT INJURIES

(71) Applicant: Icahn School of Medicine at Mount Sinai, New York, NY (US)

(72) Inventors: Carlos L. Benitez, New York, NY (US); Caleb Lear, New York, NY (US); Jason Potter, New York, NY (US); Robert Abdallah, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1200 days.

(21) Appl. No.: 16/302,412

(22) PCT Filed: May 23, 2017

(86) PCT No.: PCT/US2017/034052
§ 371 (c)(1),
(2) Date: Nov. 16, 2018

(87) PCT Pub. No.: WO2017/205411
PCT Pub. Date: Nov. 30, 2017

(65) Prior Publication Data
US 2019/0216361 A1 Jul. 18, 2019

Related U.S. Application Data

(60) Provisional application No. 62/340,331, filed on May 23, 2016.

(51) Int. Cl.
*A61B 5/00* (2006.01)
*A61B 5/055* (2006.01)

(52) U.S. Cl.
CPC ............ *A61B 5/055* (2013.01); *A61B 5/6829* (2013.01); *A61B 5/702* (2013.01)

(58) Field of Classification Search
CPC ........ A61B 5/055; A61B 5/6829; A61B 5/702
See application file for complete search history.

(56) References Cited

U.S. PATENT DOCUMENTS

| 8,596,145 B2 | 12/2013 | Miller et al. |
| 8,641,654 B2 | 2/2014 | Verkade et al. |
| 2008/0033579 A1 | 2/2008 | Phillips et al. |

(Continued)

FOREIGN PATENT DOCUMENTS

WO    WO 2016/025996    2/2016

OTHER PUBLICATIONS

Jones. "Design and Evaluation of The Kingston Brace," Masters Thesis, Queen's University, Kingston, Ontario, Canada, Jul. 31, 2009, pp. i-86, [retrieved on Jul. 21, 2017). Retrieved from the Internet: <URL:http://qspace.library.queensu.ca/jspui/bitstream/handle/1974/5438/Jones_Simon_A_200907_MScEng.pdf?sequence=1http://docs.sony.com/release/BDPS500.pdf>.

(Continued)

*Primary Examiner* — Rochelle D Turchen
(74) *Attorney, Agent, or Firm* — Leason Ellis LLP

(57) ABSTRACT

An imaging compatible device for applying a plurality of different loads to a foot for evaluating the Lisfranc joint of a patient is configured to move the ball of the foot in an axial direction, a lateral direction, and a torsional direction to assess a state of the Lisfranc joint.

32 Claims, 15 Drawing Sheets

(56) References Cited

U.S. PATENT DOCUMENTS

| | | |
|---|---|---|
| 2012/0150086 A1 | 6/2012 | Cohen |
| 2013/0204119 A1* | 8/2013 | Coelho Do Sameiro Espregue Mendes ................ A61B 5/103 |
| | | 600/595 |
| 2014/0260701 A1 | 9/2014 | Imhauser |
| 2016/0334479 A1* | 11/2016 | Poole .................. A61B 5/7203 |

OTHER PUBLICATIONS

Rossi et al. "WAKE-Up: a Wearable Ankle Knee Exoskeleton," 2014 5th IEEE International Conference on Biomedical Robotics and Biomechatronics (BioRob), Aug. 15, 2014. Sao Paulo, Brazil, pp. 504-507, [retrieved on Jul. 21, 2017]. Retrieved from the Internet: <URL:https://elearning2.uniroma1.it/pluginfile.php/237480/mod_resource/content/2/IEEE%20International%20Conference%20on%20Biomedical%20Robotics%20and%20Biomechatronics.pdf>.

\* cited by examiner

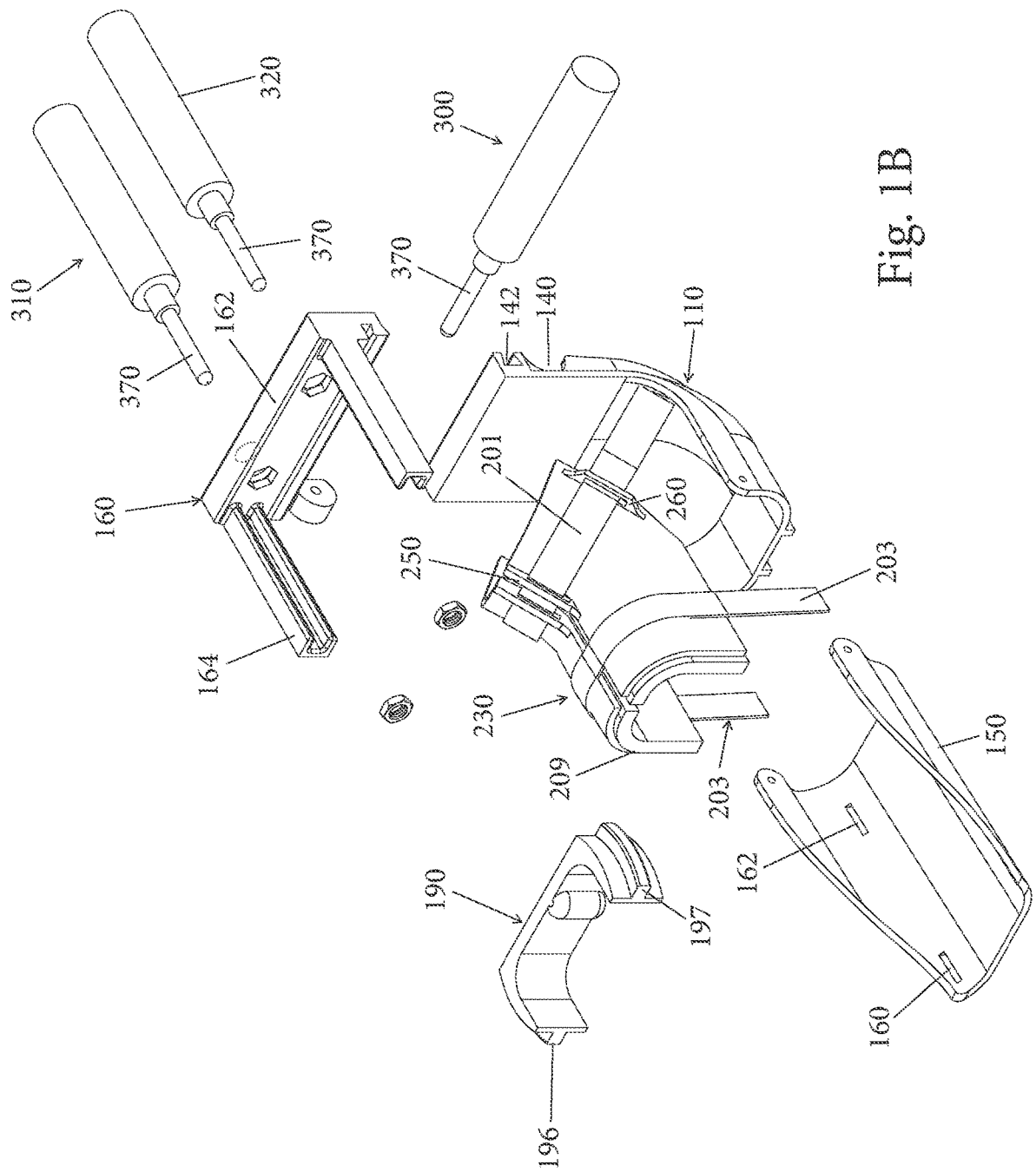

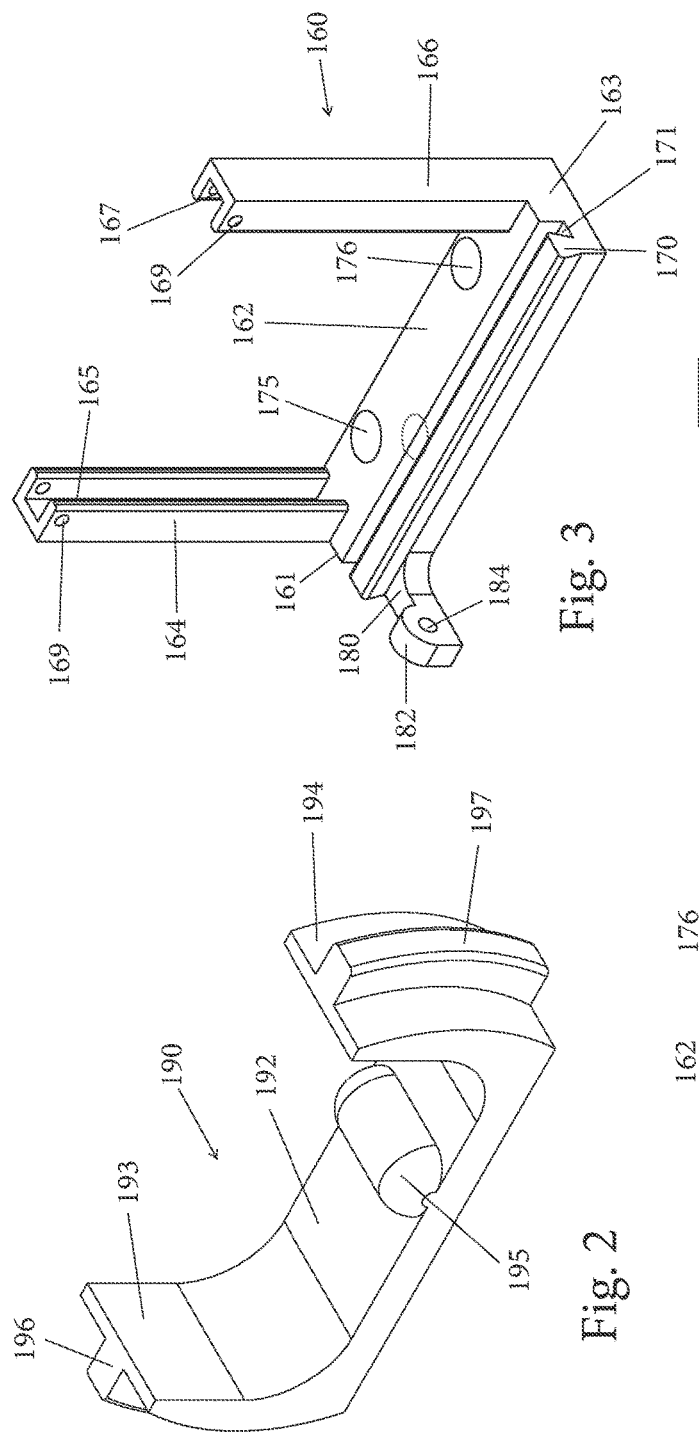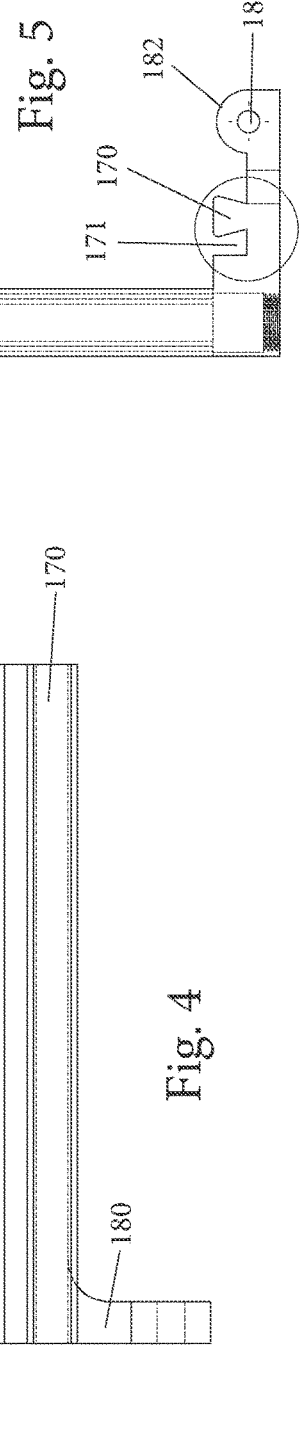

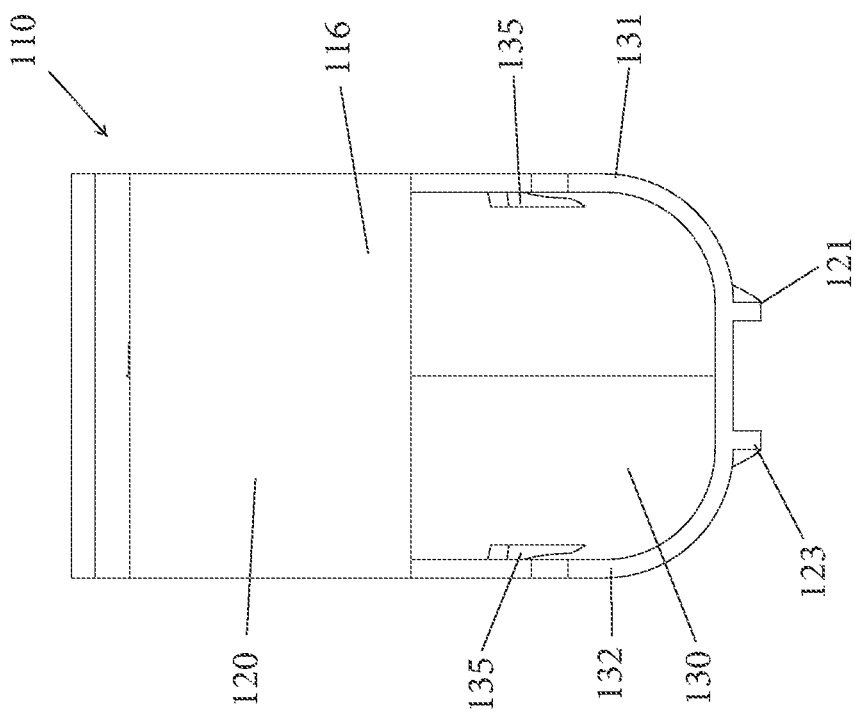
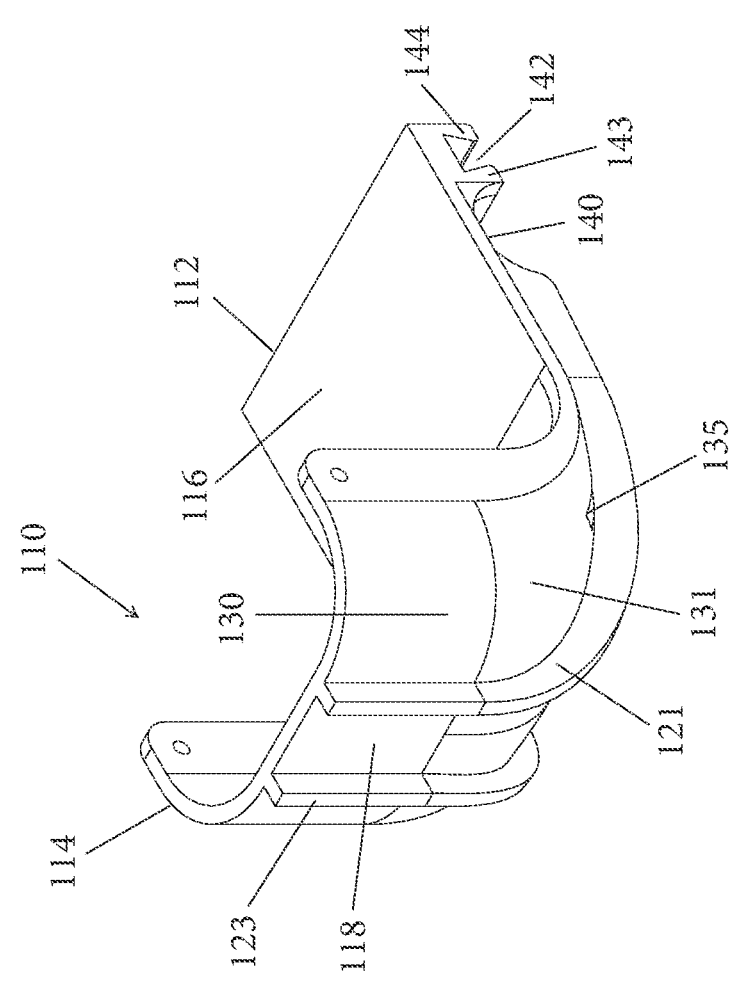

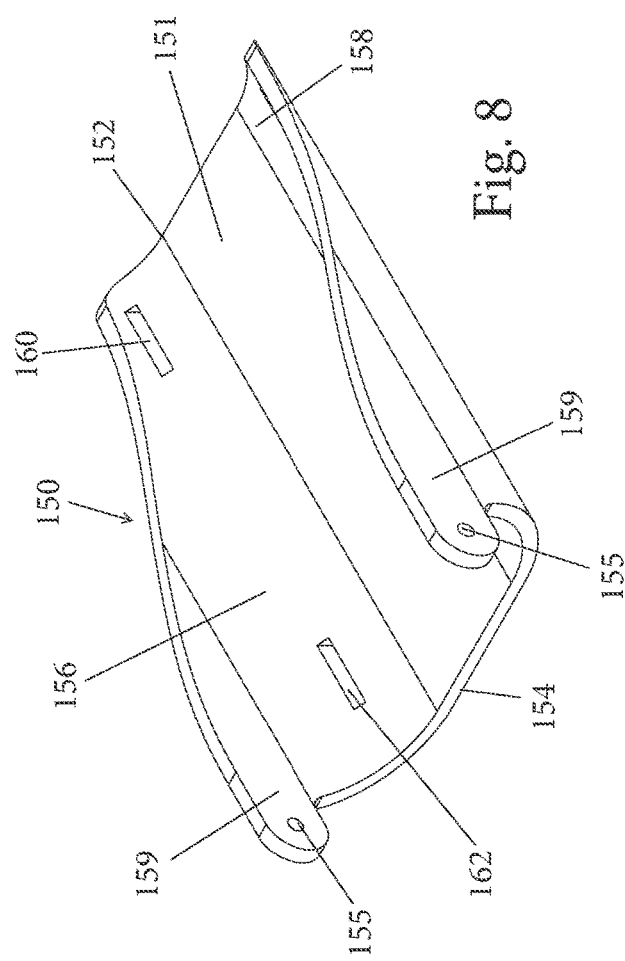
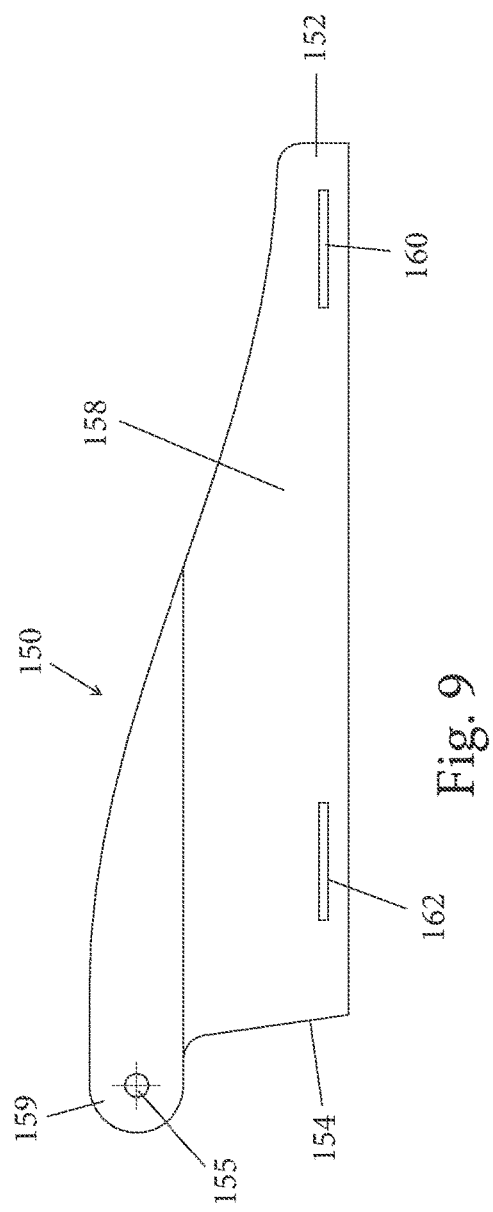

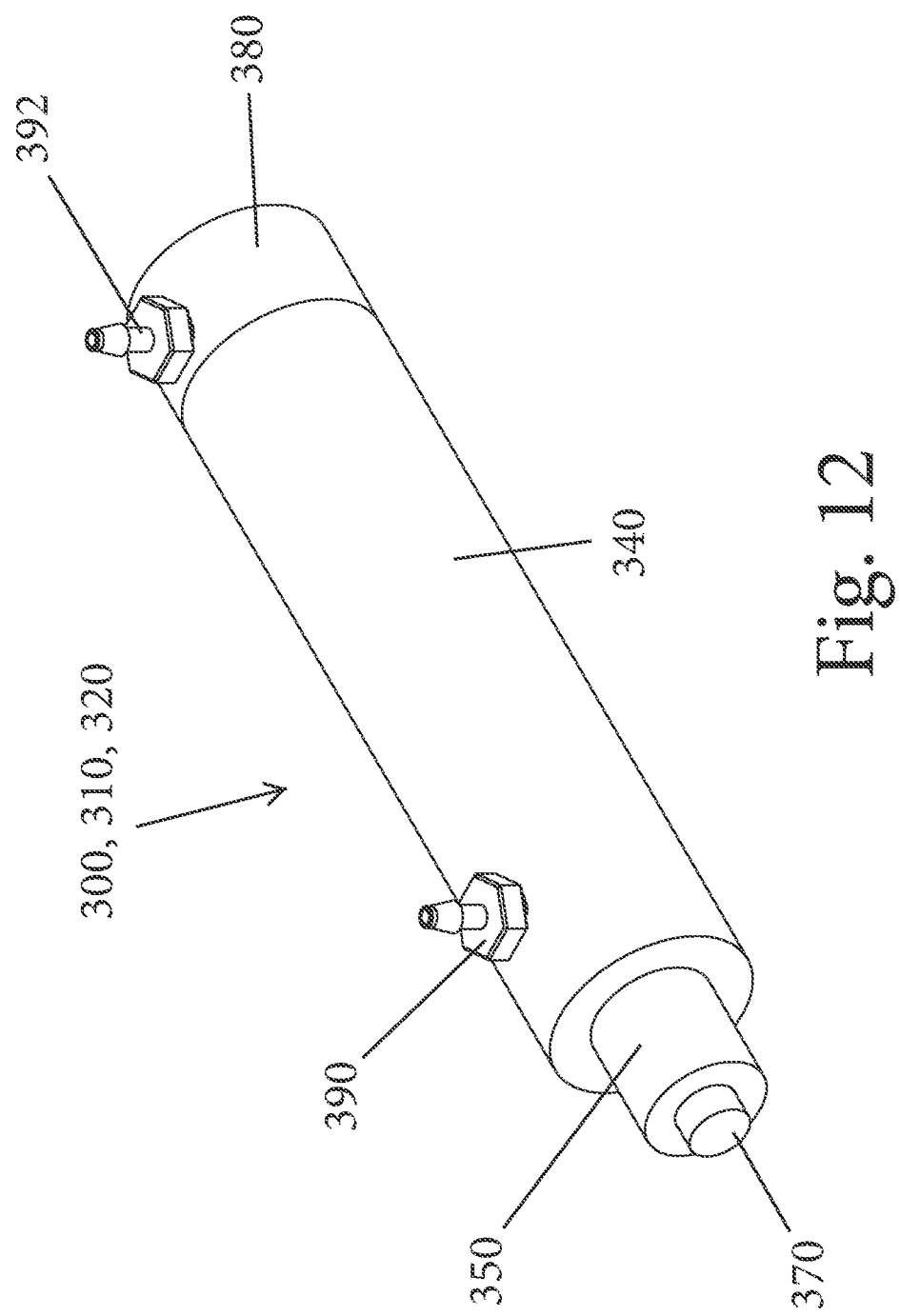

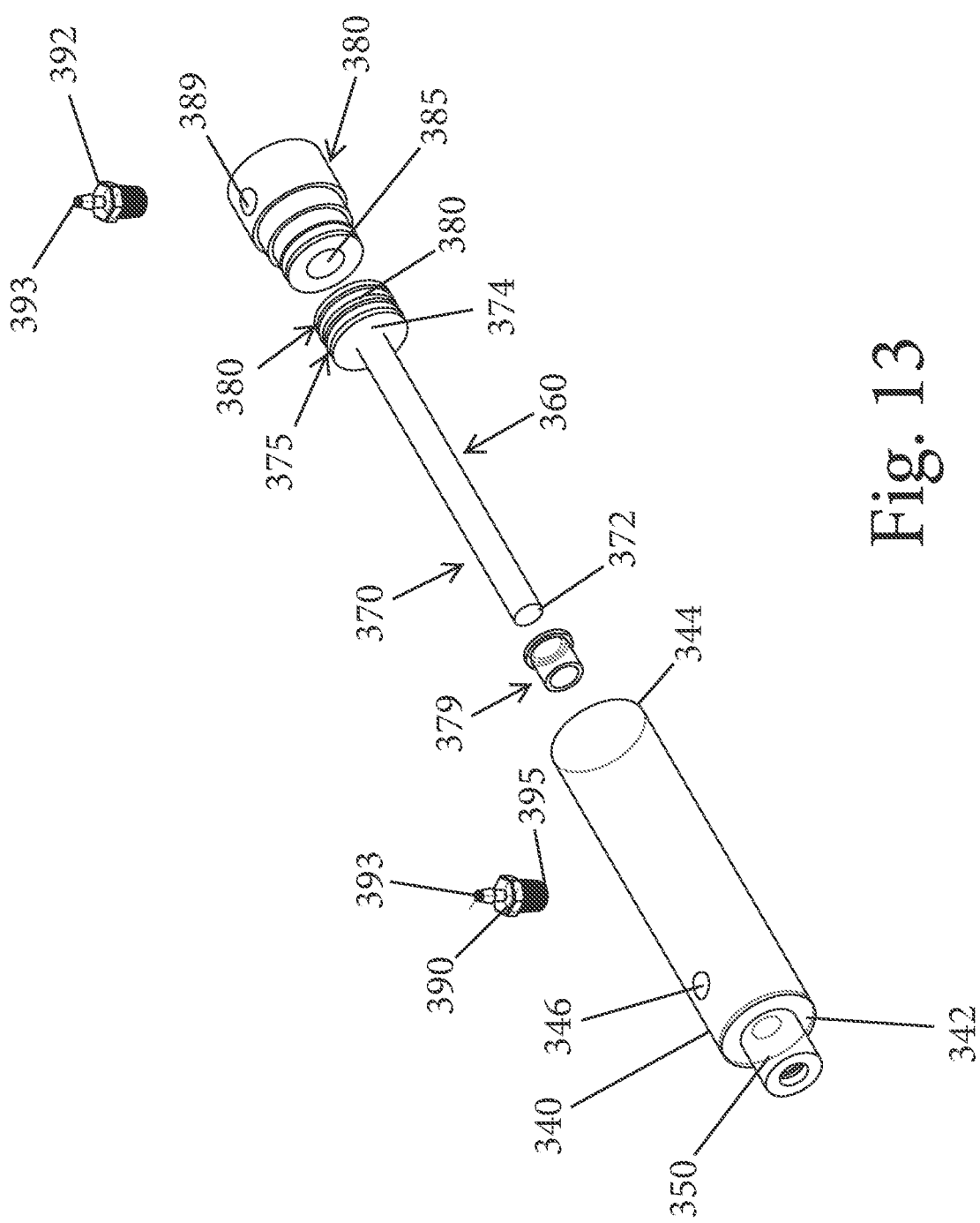

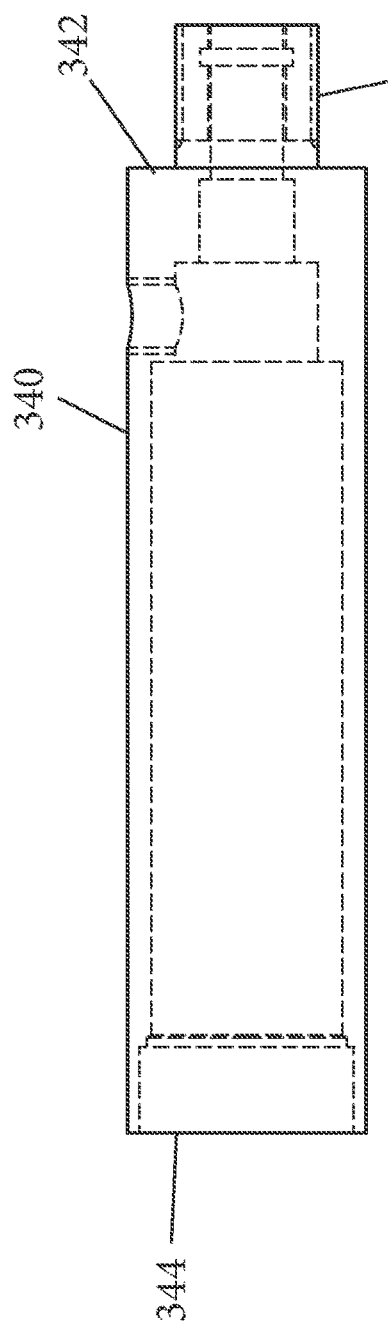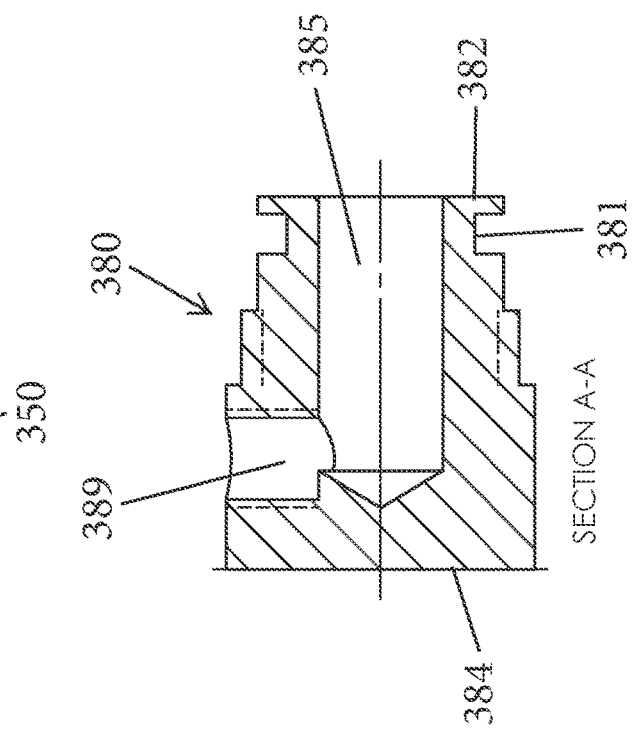

IMAGING COMPATIBLE FOOT STRESSOR FOR USE IN DIAGNOSING FOOT INJURIES

CROSS-REFERENCE TO RELATED APPLICATION

The present invention application is a U.S. National Phase Application under 35 U.S.C. § 371 of International Patent Application No. PCT/US2017/034052, filed May 23, 2017, which claims priority to U.S. patent application Ser. No. 62/340,331, filed May 23, 2016, all of which are hereby incorporated by reference as if expressly set forth in their respective entireties herein.

TECHNICAL FIELD

The present invention is related to medical diagnostic equipment and more specifically, is directed to an imaging-compatible device (foot stressor) that is for use in diagnosing foot injuries and more particularly, to an foot stressor that is configured to diagnose Lisfranc joint injuries by applying different loads to the foot in a fully controlled manner.

BACKGROUND

Midfoot injuries are painful and potentially debilitating. Diagnosis is difficult, so patients do not receive appropriate treatment or receive unnecessary surgery. The diagnosis process can be improved by performing stress tests on the foot in an imaging device, such as a magnetic resonance imaging (MRI) or a computed tomography (CT) machine.

Like the keystone of an arch, the Lisfranc joint complex (LJC) provides structure to the arch of the foot and is integral to the foot's ability to bear loads. The LJC is halfway between the toes and heel, joining the 5 metatarsals to the 3 cuneiforms and the cuboid. Strong ligaments normally prevent any motion, or laxity, between any of the 9 bones. The Lisfranc ligament is a specific ligament that joins the second metatarsal to the first cuneiform, and is where most midfoot injuries occur.

Lisfranc injuries are uncommon because they only happen in certain loading cases, usually in high energy accidents. For example, the foot of a football player on his toes is at risk of buckling under the weight of another player. Other common accidents include a gymnast slipping off a balance beam, a brake pedal breaking the foot in a car accident, or a horseback rider getting a foot caught in a stirrup. Slips, trips, and falls also cause Lisfranc injuries, though rarely. Lisfranc injuries afflict 1 in every 55,000 people per year, but are more common among active people and are the second most common foot injuries among athletes.

Injuries to the LJC are extremely painful. Patients will experience pain and swelling in the middle of the foot and usually cannot bear loads on the foot. Football players may complain of being unable to "push off" on the field. A Lisfranc injury may include a partial or complete tear of the Lisfranc ligament and the unnatural spreading of the metatarsals. Any relative displacement between bones in the LJC, a state called instability, must be treated with surgery. Typically, bones are held together with screws until ligaments heal or fused together permanently.

Lisfranc injuries are difficult to diagnose even with modern radiology. An orthopedic surgeon usually starts with a high level of suspicion based on symptoms and the nature of the accident. Then, the traditional approach is to try to isolate the joint in a physical examination. The surgeon applies axial, lateral, and twisting (torsional) stresses to the ball of the foot while tightly holding the ankle, feeling for movement between the bones of the LJC. Usually, the movement is too small to feel. Next, the surgeon orders an MRI, looking for evidence of a tear of the Lisfranc ligament or instability of the joint. In the case of an incomplete tear, doctors can see only fluid buildup in the injury site, called edema. The ligament appears grey and blurry in the MR image instead of black and well-defined. The bones may appear aligned even if the joint is instable because the foot is at rest. Of Lisfranc injury cases with MR images, one in five are initially misdiagnosed with long term consequences for the patient. Patients have gone into surgery based on an MRI of the injury, only to find that surgery is not required. Other radiological tests, such as X-rays, may be ordered; however, these tests likewise have limitations.

There is therefore a need for a device that combines a stress examination with an imaging device that allows the scope of the injury to be more clearly revealed so that patients get the proper care and treatment that they need.

SUMMARY

In one embodiment, a device for applying a plurality of different loads to a foot for diagnosing a foot injury of a patient includes a main body that is configured to receive and hold the foot and lower leg of the patient. A force application mechanism is configured to apply a plurality of different loads to the patient's foot, wherein one or more loads can be applied to the foot at a given time. The device also includes a plurality of actuators for controllably moving the force application mechanism so as to apply the one or more loads to the foot. Preferably and as described in detail below, the device is entirely made of components that are MRI or CT compatible to permit use in an MRI or CT machine.

In one exemplary embodiment, an MRI-compatible device for applying a plurality of different loads to a foot for evaluating the Lisfranc joint of a patient includes a base that is configured to receive and hold the foot and lower leg of the patient. The device also includes a force application assembly that is configured to apply the plurality of different loads to the patient's foot. The force application assembly is configured such that one or more loads can be applied to the foot at a given time, with the plurality of different loads including an axial load, a lateral load, and a torsional load (supination).

The force application assembly comprises a support member that is slidably coupled to the base for delivering a lateral load to a ball of the foot and a saddle against which the ball of the foot is placed. The saddle is coupled to and carried by the support member such that the saddle can move in an axial direction within the support member for applying an axial load to the ball of the foot and can move in a torsional direction within the support member for applying a torsional load to the foot. The device also includes a plurality of actuators for controllably moving the force application assembly relative to the base. The plurality of actuators including a first actuator for driving the support member in a lateral direction to apply the lateral load to the ball of the foot and second and third actuators that drive the support member to allow both the axial load and the torsional load to be applied to the ball of the foot depending upon the actuation state of each of the second and third actuators.

When MRI is used to assess the extent of the foot injury, a traditional diagnosis is based on a single MRI test which may not show the true extent of the injury. The present method allows a surgeon to compare up to six sets of images in varied states of stress. More data leads to a more informed diagnosis, ensuring that patients get the care they need.

In addition, unlike other traditional devices, the present device does not require the patient to be repositioned to conduct the various load tests on the foot. Moreover, multiple loads can be applied to the foot at the same time something which is not possible with other traditional devices.

In one embodiment, the present device used a building air supply to actuate pneumatic pistons which are used as the first, second and third actuators. A surgeon in the control room uses of a set of valves to choose the direction of the forces and slowly raises the pressure until the patient in the MRI machine can feel it. Remote actuation saves time during the exam, allowing the surgeon to take more tests during a single appointment.

BRIEF DESCRIPTION OF THE DRAWING FIGURES

FIG. 1B is an exploded perspective view a foot stressor in accordance with another exemplary embodiment of the present invention;

FIG. 2 is a perspective view of a saddle part of the foot stressor;

FIG. 3 is a perspective view of a support part of the foot stressor;

FIG. 4 is a plan view of the support part;

FIG. 5 is a side elevation view of the support part;

FIG. 6 is a perspective view of a base part of the foot stressor;

FIG. 7 is a plan view of the base part;

FIG. 8 is a perspective view of a brace part of the foot stressor;

FIG. 9 is a side elevation view of the brace part;

FIG. 12 is a perspective view of a cylinder of the foot stressor in an assembled condition;

FIG. 13 is an exploded view of the cylinder;

FIG. 14 is a side view of a cylinder body of the cylinder;

FIG. 15 is an end view of a cylinder end cap of the cylinder;

FIG. 16 is a cross-sectional view of the cylinder end cap;

DETAILED DESCRIPTION OF CERTAIN EMBODIMENTS

FIGS. 1-16 illustrate a device 100 for applying multiple different loads to a patient's foot for diagnosing a foot injury according to a first exemplary embodiment of the present invention. The device 100 is also referred to herein as a foot stressor 100 and is configured such that it is compatible with imaging devices, such as an MRI device or CT scan, and in particular, is configured to diagnose Lisfranc joint injuries. As described herein, the device 100 is configured to have three degrees of freedom (i.e., axial, lateral, torsional) which allows an axial load, a lateral load, and/or a torsional load to be applied to the foot.

As discussed herein, the device 100 is compatible with imaging devices in that the device 100 can both be safely used in an imaging device environment and is at least substantially invisible under imaging visualization (e.g., MRI visualization, CT scan, etc.). In other words, the presence of the device 100 does not distort the imaging of the foot (does not produce image artifacts). The materials used to form each of the components of the device 100 must thus be compatible and safe for use in imaging equipment. To imaging devices, there is a significant difference between ferromagnetic materials and non-ferromagnetic materials. In terms of metals, there are thus ferromagnetic metals and non-ferromagnetic metals. In an MRI suite, a concerted effort is made to rid the area of ferromagnetic materials and use non-ferromagnetic replacements whenever possible. Non-ferromagnetic metals include aluminum, titanium, brass, copper, and many others. These (and other) non-ferromagnetic metals can present other problems and hazards during MRI imaging and since it is remarkably difficult to distinguish magnetically 'safe' metals from magnetically 'unsafe' metals, MRI facilities must assume all metals to be magnetically unsafe unless and until they've been verified to be non-magnetic.

The device 100 is therefore constructed from non-ferromagnetic materials, including but not limited to safe metals, wood, plastics, etc. The device 100 therefore complies is preferably constructed to comply with applicable standards and test methods concerning the use of equipment in an imaging environment. For example, ASTM 2052 is a test method that is required to determine if the presence of a medical device may cause injury to individuals during an MR examination and in the MR environment. Other safety issues which should be addressed include but may not be limited to magnetically induced torque (see Test Method F2213) and RF heating (see Test Method F2182) (F2182—measurement of radio frequency (RF) induced heating on or near a passive medical implant).

Figure 1A:
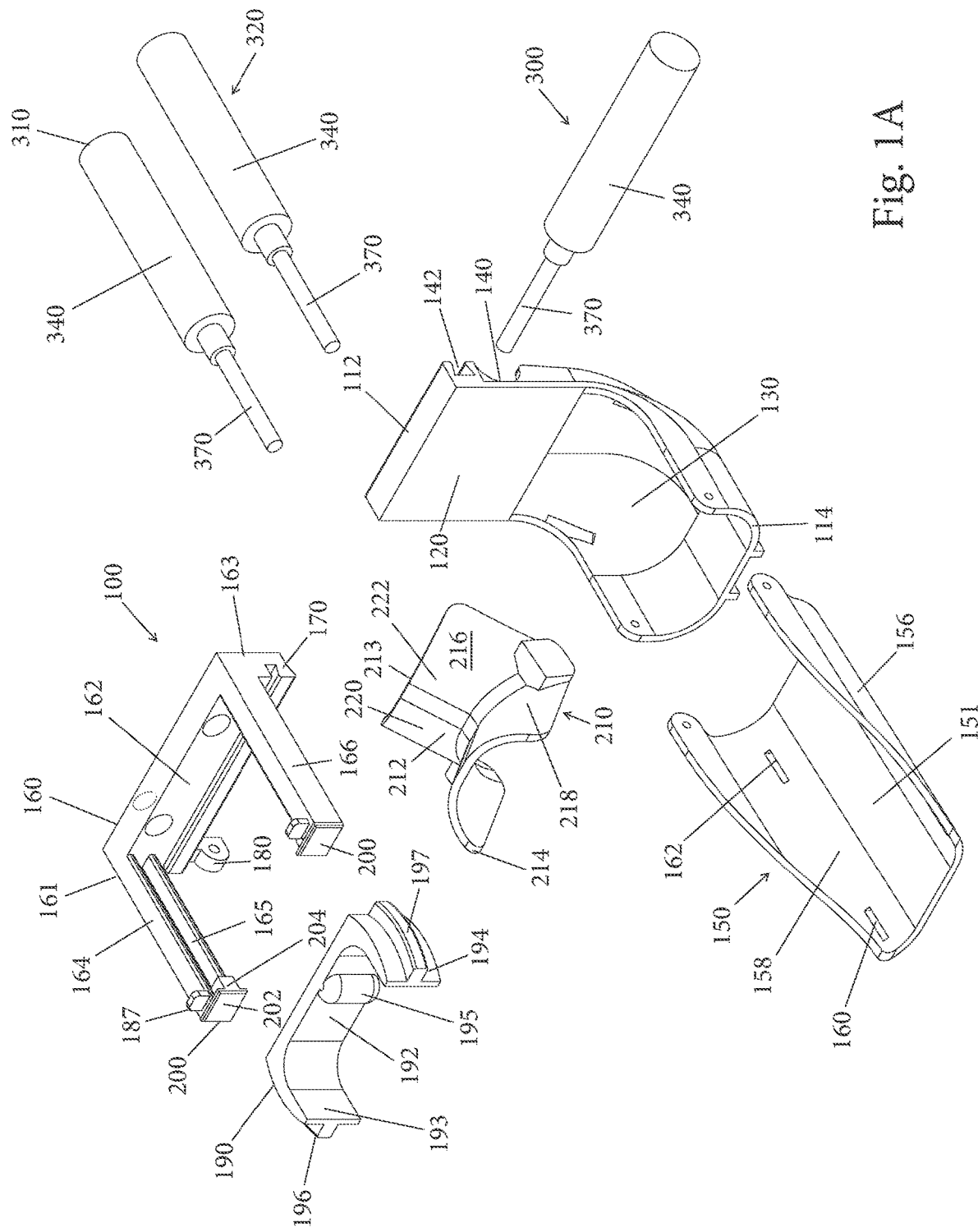
FIG. 1A is an exploded perspective view a device for applying multiple different loads to the foot (foot stressor) for diagnostic purposes in accordance with one exemplary embodiment of the present invention.

As shown in the exploded view of FIGS. 1A and 1B, the foot stressor 100 is formed of a number of parts that are assembled together to form the foot stressor 100. The foot stressor 100 is formed of a base 110 that supports the foot and positions the foot in the imaging equipment, such as an MRI coil. As shown in FIGS. 1, 6, and 7, the base 110 comprises a curved structure that has a first end 112 and an opposing second end 114. The base 110 also includes a first face 116 and an opposing second face 118. Due its curved nature, the base 110 can generally be considered to have an elbow shape.

The base 110 has a first portion 120 that terminates at the first end 112 and a second portion 130 that terminates at the second end 114. The first portion 120 represents one leg of the base 110, while the second portion 130 represents the other leg of the base and the first and second portions 120, 130 have different shapes. The first face 116 represents the surface against which the patient's foot is placed during use of the foot stressor 100 and therefore, the first face 116 is generally a smooth surface. As shown, the first portion 120 is a substantially planar section, while the second portion 130 is a curved section. As shown, the second portion 130 is also concave shaped in that it includes side walls 131, 132 that are also curved. The innermost sections of the side walls 131, 132 are parallel to one another and include a pair of holes 133 that are spaced apart and axially aligned with one another. The first portion 120 does not include side walls.

As shown in FIG. 7, the second portion 130 does include a pair of openings or slots 135 that are formed in and pass through the opposing side walls 131, 132. The openings 135 can thus be elongated (generally rectangular) in shape and can be formed along a curved portion of the second portion 130.

The second face 118 which faces away from the patient's foot includes a number of integral features in contrast to the generally smooth surface of the first face 116. For example, the second face 118 includes a pair of upstanding rails 121, 123 that extend from the second end 114 to the first portion 120. The rails 121, 123 are spaced apart from one another and run parallel to one another along a portion of the second face that terminates at the second end 114 and then taper outwardly as the rails 121, 123 progress toward the first portion 120 (resulting in the distance between the rail 121, 123 becoming greater in the direction toward the first portion 120). In fact, the rails 121, 123 can define two opposing side walls of the first portion 120. As shown, at the second end 114, the two rails 121, 123 can be spaced the same distance from a center point of the second face 118. Each rail 121, 123 can have any number of different shapes with the illustrated rails 121, 123 having a square shaped cross-section.

The second face 118 of the first portion 120 includes a number of coupling features that allow other parts to be detachable secured to the base 110 as described herein. For example, along the second face 118, the first portion 120 includes a first opening 140 that extends across (transversely) the width of the first portion 120. The first opening 140 can have an arcuate shape and is partially defined by free ends of the rails 121, 123.

The second face 118 also includes a dove tail shaped joint structure including a tail 142 (notch). The tail 142 has a trapezoidal shape defined by a pair of angled walls 143, 144. Like the first opening 140, the tail 142 also extends across (transversely) the width of the first portion 120. The tail 142 is thus located adjacent the first opening 140 and is located closer to the first end 112 compared to the first opening 140. It will therefore be appreciated that the angled wall 143 in combination with the free ends of the rails 121, 123 define the first opening 140. An outer exposed surface of the angled wall 144 thus defines the first end 112 of the base 110 and can be a flat surface.

Referring to FIGS. 1A, 1B, 8 and 9, the foot stressor 100 also includes a brace component or part 150 that is configured to be coupled to the base 110 to define an upper boot-like structure in which the foot of the patient is received. The brace 150 prevents the ankle and heel from moving during the imaging procedure. The brace 150 has a first end 152 and an opposing second end 154. The brace 150 is also a curved part that is configured to mate with the curved section of the second portion 130 of the base 110 and in fact, the brace 150 is intended to be coupled to the base 110. As described herein, the coupling between the brace 150 and the base 110 can be of a fixed nature.

Similar to the base 110, the center section 151 of the brace 150 can be a flat section, while sides of the brace 150 are defined by opposing curved side walls 156, 158 that are located on either side of the flat center section 151. Each of the side walls 156, 158 includes an extension (tongue) 159, at the second end 154, that projects forward of the end of the center section 151 and the ends of the side walls 156, 158. Each extension 159 includes a hole 155 with the holes 155 of the two extensions 159 being opposite one another and are axially aligned. As illustrated, the second end 154 is intended to abut or be placed in close proximity to the second end 114 of the base 110.

The extensions 159 are configured to be placed on the outside of the side walls 131, 132 of the second portion 130 and more specifically, the extensions 159 are positioned along the outer surfaces of the side walls 131, 132 with the holes 155 of the extensions 159 being axially aligned with the holes 133 of the side walls 131, 132. A coupling member (not shown) is received with one set of holes 133, 155 and another coupling member (not shown) is received within the other set of holes 133, 155 for securely coupling the brace 150 to the base 110. As mentioned herein, the coupling between the brace 150 and the base 110 can be of a type that allow the brace 150 to bend slightly (i.e., allows for pivotal adjustment of the brace 150 relative to the base 110 so as prevent snapping of the brace 150 under stresses of the leg). The coupling members between the brace 150 and the base 110 can take any number of different forms including but not limited to fasteners, such as pins, bolts, etc.

Each of the side walls 156, 158 includes a pair of slots that define two pairs of opposing slots. More specifically, a first pair of slots 160 is formed spaced from but proximate the first end 152 and a second pair of slots 162 are formed spaced from but proximate the second end 154. The first pair of slots 160 is formed opposite one another and the second pair of slots 162 is formed opposite one another. The first and second pairs of slots 160, 162 can have any number of different shapes and in the illustrated embodiment, the first and second pairs of slots 160, 162 are rectangular shaped.

The brace 150 thus further extends the second leg (second portion 130) of the base 110 and is intended to be placed behind the lower leg below the knee of the patient (e.g., along the calf of the patient). The brace 150 thus reaches mid-calf and serves to stabilize the leg by distributing the weight of the foot stressor 100 to the leg rather the ankle (as would be case if the brace 150 was not present).

The foot stressor 100 also includes a column support or slider 160 that is configured to mate with the base 110 as shown in FIGS. 1A, 1B, and 3-5. The column support 160 is configured to displace the joint laterally. The column support 160 includes an end wall 162 that has a first end 161 and an opposing second end 163. The column support 160 has a first column or first leg 164 that is located at the first end 161 and a second column or second leg 166 that is located the second end 163. The first and second columns 164, 166 are preferably integrally formed with the end wall 162 that extend between the first and second columns 164, 166. The first and second columns 164, 166 define longitudinal tracks 165, 167 and in particular, each of the first and second columns 164, 166 can be in the form of C-shaped structure with the openings into the longitudinal tracks defined between the opposing side walls of the column facing one another. Proximate a free end thereof, each of the first column 164 and the second column 166 includes a pair of holes 169. In particular, each of the opposing side walls of each of the first column 164 and the second column 166 includes a pair of opposing holes 169 that are axially aligned.

As shown, the first column 164 is located in one corner of the end wall 162 and the second column 166 is located in another corner of the end wall 162.

The end wall 162 also includes a dovetail pin or protrusion 170 that is configured to mate with and be received within the tail 142. The dovetail pin 170 is defined by a pair of angled walls such that the dovetail pin 170 has a trapezoidal shape. A space 171 is formed between the dovetail pin 170 and a base portion of the end wall 162 from which the first column 164 and second column 166 protrude.

The column support 160 also includes a protrusion 180 that is formed at the first end 161 and protrudes outwardly from an outer wall that defines the dovetail pin 170. The protrusion 180 can be in the form of a finger that is formed locally as shown in FIGS. 3-4. Due to its localized formation, the protrusion 180 does not extend along the entire length of the dovetail pin 170 but is only formed at one end thereof. The protrusion 180 has an upstanding tab portion 182 that includes a central through hole 184. The top surface of the upstanding tab portion 182 can be rounded (e.g., semicircular in shape). An axis passing through the center of the though hole 184 is thus oriented parallel to a longitudinal axis of the end wall 162 with longitudinal axes of the first and second columns 164, 166 being oriented perpendicular thereto. As shown in FIG. 5, the through hole 184 generally lies below the dovetail pin 170.

The end wall 162 has a first through hole 175 and a second through hole 176 which is spaced from the first through hole 175. The first and second through holes 175, 176 are thus formed between the first and second columns 164, 166. The illustrated first and second through holes 175, 176 have circular shapes; however, other shapes are equally possible.

The foot stressor 100 also includes a saddle 190 that is configured to mate with the column support 160 and represents a part of the foot stressor 100 that receives the forefoot. The saddle 190 is configured to concentrate forces to the ball of the foot. As described herein, the saddle 190 engages the first and second columns 162, 164 such that the saddle 190 sides and travels in between the two columns. The saddle 190 incudes a center section 192 and first and second upstanding end portions 193, 194 (end walls) that project away from the center section 192. As illustrated, the saddle 190 can be symmetric in shape and the end portions 193, 194 are mirror images of one another. The end portions 193, 194 can have curved shapes that curve inwardly toward one another. Outer surfaces of the end portions 193, 194 include rails 196, 197 that are configured to be received within the longitudinal tracks 165, 167 of the first and second columns 164, 166, thereby coupling the saddle 190 to the column support 160.

The rails 196, 197 can also be curved due to the curved nature of the end portions 193, 194. The rails 196, 197 can have any number of shapes so long as they complement the longitudinal tracks 165, 167 and allow the saddle 190 to be securely yet movably coupled to the column support 160. A friction fit can be formed between the saddle 190 and the column support 160. As will also be appreciated based on the following discussion, the curved shape of the rails 196, 197 allow one end of the saddle to be displaced relative to the other end (See FIGS. 23-25 and the discussion thereof) (e.g., one end is raised relative to the other end). In other words, in one operating move of the foot stressor 100, the saddle is rocked between the first and second columns 164, 166 without causing a disengagement between the saddle 190 and the column support 160.

In addition, the inner face of the center section 192 includes a raised bump 195 that is formed at an off-center location and can generally have a semi-circular shape with rounded ends (e.g., oblong shaped). However, other shapes are equally possible for the bump 195. The formation of the bump 195 at an off-centered location causes the saddle 190 to have an asymmetrical shape. The bump 195 is formed at a location that corresponds to the second metatarsal of the foot so as to pre-stress the Lisfranc joint when the patient's foot presses against the center section 192 of the saddle 190.

The column support 160 also includes a pair of end caps 200 that are configured to cover the free ends of the first and second columns 164, 166. The end cap 200 has an enlarged outer portion 202 to allow the end cap 200 to be easily grasped and manipulated. The end cap 200 also include an inner portion 204 that projects inwardly from the outer portion 202 and has smaller dimensions such that the end cap 200 can be thought of as being T-shaped. The inner portion 204 is configured to be inserted into one of the longitudinal track 165, 167. The outer portion 202 seats against the end of the first and second columns 164, 166 due to its enlarged size and therefore, closes off the ends of the first and second columns 164, 166. The end caps 200 serve to restrict and limit the degree of travel of the saddle 190. In other words, the end caps 200 limit the maximum axial motion of the saddle 190 and prevents the saddle 190 from falling out of the longitudinal tracks 165, 167.

In addition, a pair of fasteners 187 can be provided and configured to be received within the holes 169 formed through each of the first column 164 and the second column 166. The fasteners 187 can take any number of different forms including but not limited to a pin, a screw, etc. that are configured to extend across one of the respective longitudinal tracks 165, 167. The fasteners 187 serve to hold the end caps 200 in place at the ends of the first and second columns 164, 166.

The column support 160 is also configured to mate to and securely attach to the base 110 at the first end 112 thereof. Any number of techniques can be used to couple the end wall 162 of the column support 160 to the first portion 120 of the base 110. In the illustrated embodiment, a dovetail joint can be formed between the column support 160 and the base 110; however, it will be understood that this is merely one exemplary technique for coupling the column support 160 to the base 110 and other techniques are equally possible. To form the dovetail joint, the dovetail pin 170 is inserted into the tail 142 and one of the column support 160 and the base 110 is slid relative to the other causing the dovetail pin 170 to increasingly travel within the tail 142 until the column support 160 is completely and interlockingly attached to the base 110.

As will be appreciated in view of the discussion herein, the coupling between the column support 160 and the base 110 must be of a type that allows for lateral movement (sliding action) of the column support 160 relative to the base 110. The dovetail joint described above allows for sliding of the column support 160 within and relative to the base 110.

Figure 11:
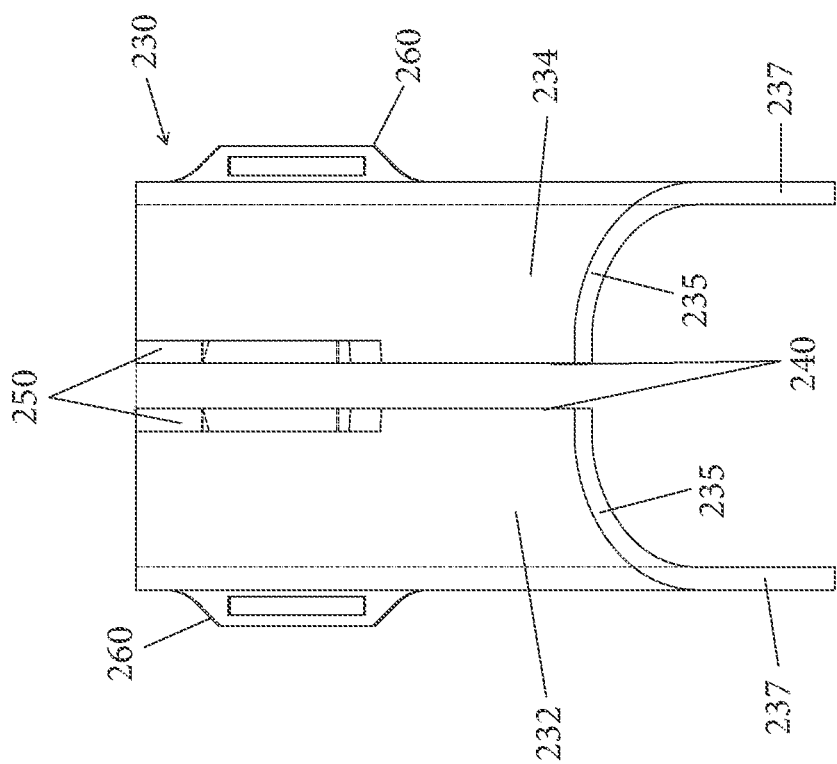
FIG. 11 is a plan view of the clamp part of FIG. 1B.
Figure 10:
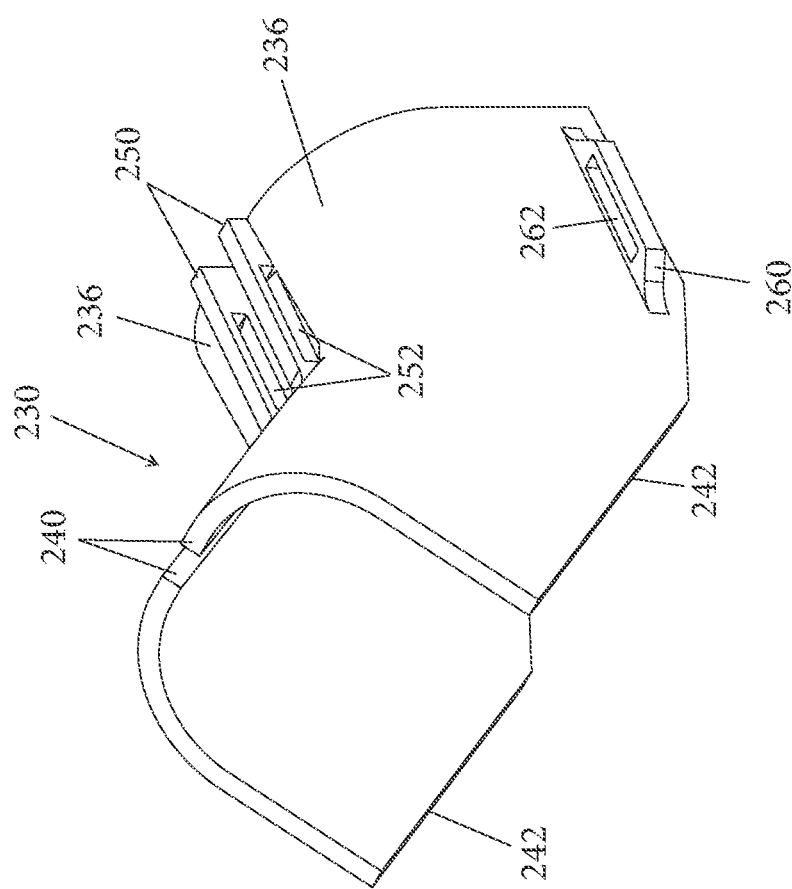
FIG. 10 is a perspective view of a clamp part of the foot stressor of FIG. 1B.

The foot stressor 100 also includes a clamp that is intended to be placed along the front of the lower leg of the patient when the patient's foot is contained with the foot stressor 100. The clamp is also configured to mate with the base 110 and the brace 190 as described below so as to securely hold the patient's leg in place and tightly hold bones proximal to the joint (Lisfranc joint). FIG. 1A illustrates one clamp 210, while FIGS. 1B, 10 and 11 illustrate another clamp 230. Both clamps 210, 230 are constructed to perform the same function set forth above.

The clamp 210 is formed of a body 212 that has a first end 213 and an opposing second end 214. The body 212 has a first (forward) portion 216 and a second (rear) portion 218 with the two portions 216, 218 being angled with respect to one another. The first portion 216 is intended for placement above the lower leg of the patient, while the second portion 218 is intended for placement over the top of at least a portion of the patient's foot. More specifically, the clamp 210 covers the ankle and the foot up to the Lisfranc joint. The clamp 210 is split down the center so as to define a first clamp half 220 and a second clamp half 222. By splitting the clamp 210 down the center, a single strap can be used to clamp the foot down to the base 110 and squeeze the foot side-to-side. More specifically, an adjustable strap (e.g., a nylon strap with a fastener (hook and loop or buckle) pass through the openings/slots 135 that are formed in and pass through the opposing side walls 131, 132. The strap wraps across the top of the clamp 210 (both halves thereof) and around the backside of the base 110. The tightening of the strap causes the clamp 210 to be tightened about the patient's leg and secures the clamp 210 to the base 110.

FIGS. 1B, 10 and 11 illustrate the clamp 230 which has an alternative construction compared to the clamp 210; however, the basic functionality is the same. More specifically, the clamp 230 is also of a split design in that it is defined by a first half 232 and an opposing second half 234. Each of the first half 232 and the second half 234 is of an angled construction in that each is defined by a first (forward) portion 236 and an opposing second (rear) portion 238. Each of the first half 232 and the second half 234 is generally L-shaped in cross-section in that there is an upper portion 235 and a side wall 237. As a result when the first and second halves 232, 234 are placed together, a generally U-shaped clamp is formed. The upper portion 235 terminates at a first edge 240 (that extends from the first portion 236 to the second portion 238) and the side wall 237 terminates at a second edge 242 (that extends from the first portion 236 to the second portion 238).

Similar to the clamp 210, the clamp 230 also has a coupling feature to permit the clamp 230 to be securely attached to the base 110. More specifically, each of the first half 232 and the second half 234 includes a first coupling member 250 formed proximate to or at the first edge 240 and a second coupling member 260 formed proximate to or at the second edge 242. The first coupling member 250 can be in the form of a first flange that extends outwardly from the upper portion 235 and includes a first slot 252 that is formed therein. Similarly, the second coupling 260 can be in the form of a second flange that extends outwardly from the side wall 237 and includes a second slot 262 that is formed therein. As best shown in FIG. 11, the first and second coupling members 250, 260 and more particularly, the first slot 252 and the second slot 262 are preferably both located the same distance from the first end of the respective first half 232 or second half 234. This orientation causes the first slot 252 to be axially aligned with the second slot 262 to allow a strap to pass through the first slot 252 of the first half 232 and extend linearly to the second slot 262 of the second half 234 where it likewise passes therethrough. The strap also passes across the space between the two halves 232, 234 and then passes through both the first slot 252 of the second half 234 and the second slot 262 of the second half 234.

The first and second coupling members 250, 260 are preferably integrally formed with the remaining body of the clamp 230.

As with clamp 210, when clamp 230 is paired with the base 110, an adjustable strap 201 (e.g., a nylon strap with a fastener (hook and loop or buckle) pass through the openings/slots 135 that are formed in and pass through the opposing side walls 131, 132. The strap is fed through slot 135 of the side wall 131 the first and second slots 252, 262 of the first half 232 and then through the first and second slots 252, 262 of the second half 234 and then through slot 135 of the side wall 132. The tightening of the strap causes the clamp 230 to be tightened about the patient's leg and secures the clamp 230 to the base 110.

The clamp 230 is also releasably coupled to the brace 150 using a second strap 203 (FIG. 1B). The second strap 203 extends across the top of the two halves of the clamp 230 and can be fed through the pair of openings 162 of the brace 150.

FIG. 1B illustrates that optional inner padding 209 or the like can be disposed between the patient's leg and the clamp 230. The inner padding 209 can have a complementary shape compared to the clamp 230 and therefore, it can be of a split construction.

Figure 26:
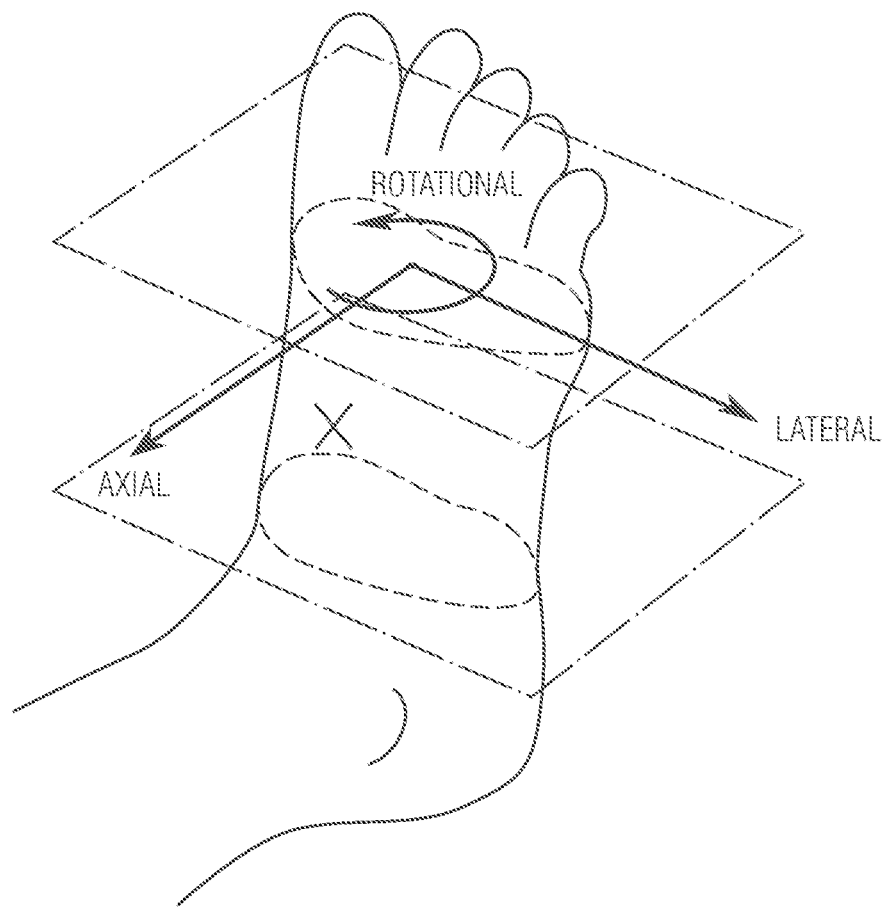
FIG. 26 is a schematic illustrating the desired motions of the foot which can be described as planar motion of the ball of the foot relative to a fixed plane proximal to the Lisfranc joint.

The foot stressor 100 is configured to controllably displace the foot in a number of different directions by applying different loads to the foot to investigate and assess Lisfranc joint injuries. FIG. 26 illustrates the desired motions of the foot can be described as planar motion of the ball of the foot relative to a fixed plane proximal to the Lisfranc joint. The primary mechanism (component) for controllably displacing the foot is the saddle 160 which can be displace the ball of the foot axially, laterally, and rotationally (torsionally). As described herein, motion of the saddle 160 is constrained to the plane by the C-shaped first and second columns 162, 164, one on either side of the foot. The dovetail joint allows for lateral motion of the saddle 160. Axial motion of the saddle 160 results when an even force (load) is applied to both ends of the saddle 160 so that the saddle 160 moves axially within the longitudinal tracks defined by the first and second columns 162, 164. Rotational motion results when an axial force (load) is applied to one end of the saddle 160 while no axial force is applied to the other end resulting in rotation of the saddle 160. In all of these movements, the degree of applied force will dictate the degree of displacement of the saddle 160. As described herein, the applied forces and thus the movements of the saddle 160 can be carefully controlled with precision by the user of the foot stressor 100.

It will therefore be appreciated that a plurality of actuators are provided for controllably moving the saddle 160 in the aforementioned manner. Any number of different types of actuators can be used to move the saddle in an axial direction, lateral direction and rotational direction. For example, hydraulic systems, non-metallic spring based systems, and push-pull cable systems are other alternatives that can be implemented to provide the plurality of actuators. As described in detail below, the plurality of actuators can be part of a pneumatic system. Pneumatics offer a number of advantages including that they can take advantage of building air, offer more flexibility in terms of the building setup than push-pull cables and fail more safely than hydraulics.

It will be appreciated that given the location of use (imaging equipment), no electronics can be used for the remote actuation.

For example and according to one embodiment, the actuators are in the form of pneumatic pistons that controllably act on and applied various forces (loads) to the saddle 160. As shown in the figures, the actuators can be in the form of a first actuator 300, a second actuator 310 and a third actuator 320 that are configured and positioned to actuate the saddle 160. The first actuator 300 corresponds to lateral motion and the second and third actuators 310, 320 are used in tandem for axial motion and in opposition for rotational motion.

Figure 27:
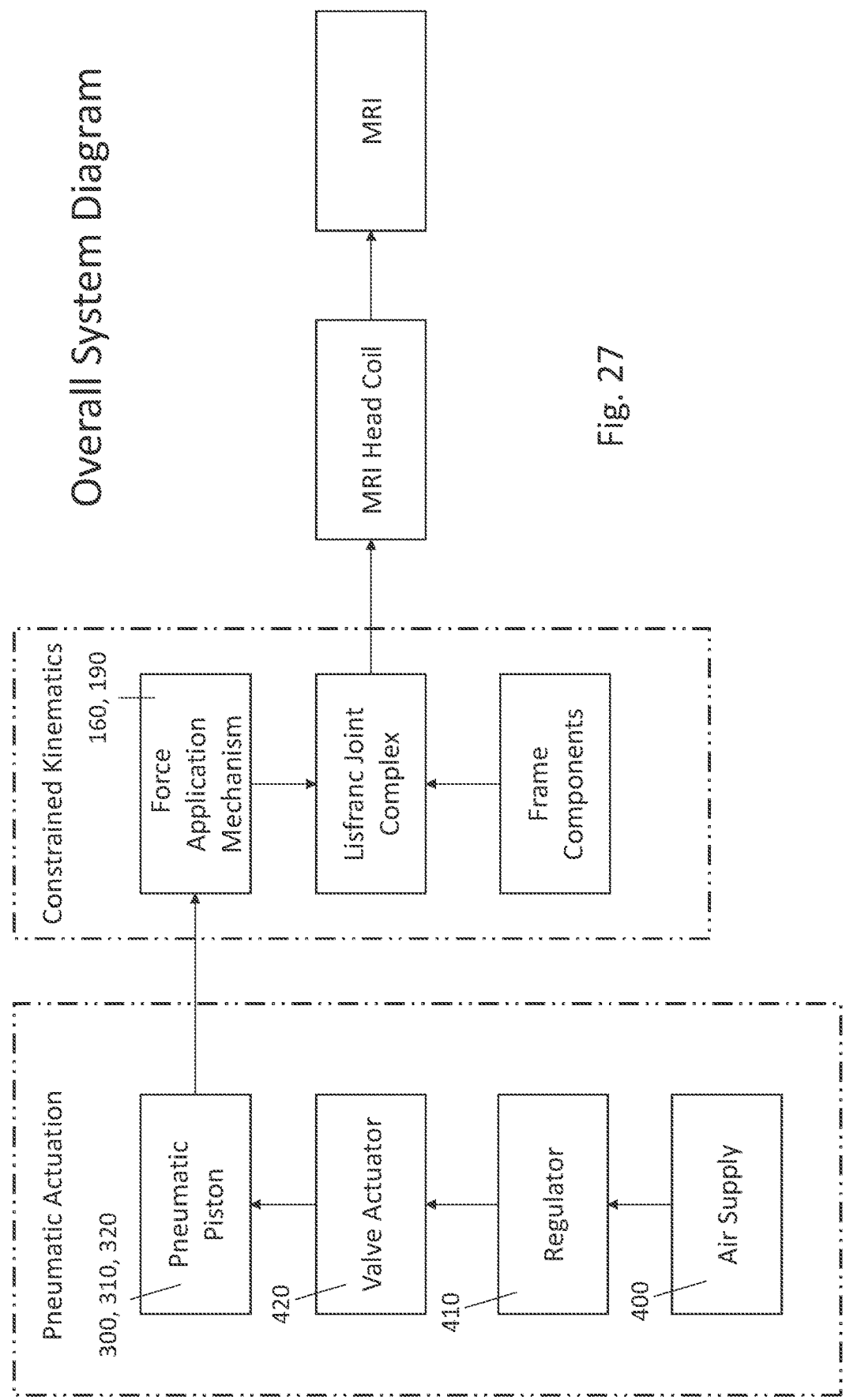
FIG. 27 is a schematic of an overall diagnostic system that incorporates the device of the present invention.

When each of the first actuator 300, second actuator 310, and third actuator 320 is in the form of a pneumatic piston, the system layout is set forth in FIG. 27 which depicts the foot stressor 100 being used in combination with an MRI head coil that is disposed within a MRI device, such as a closed, high field 1.5 Tesla MRI device. It will also be understood that during an MRI exam, foam padding or inflatable balloons are used to further stabilize the foot stressor 100 in the head coil. The head coil typically has a circular shaped hole and therefore, when the foot stressor 100 is inserted into the head coil, there is open space between the foot stressor 100 and the inner surface of the head coil. This open space is where the padding or inflatable structures, like one or more balloons, is disposed.

As shown in FIG. 27 when pneumatic actuation is used to apply forces to the foot, the pneumatic pistons 300, 310, 320 are each connected to an air (or other gas) source 400, in this case an air source. The connections are typically formed by a series of tubes that are fluidly connected between the pneumatic piston 300, 310, 320 and the air source 400. For example, ⅛ inch PVC tubing can be used. The foot stressor 100 and in particular, the pneumatic actuators thereof is controlled by a set of (manual) three-way valves 420 and a pressure regulator 410. The user (surgeon) sets the valves 420 to achieve the desired loading direction (e.g., axial, lateral or rotational) and then raises the pressure of the device by using the pressure regular 410 until the patient feels the load and the foot is displaced as described herein. The valves 420 are thus positioned so as to allow air to flow to or conversely be prevented from flowing to one or more of the pneumatic pistons 300, 310, 320. The pressure regular 410 and valves 420 are positioned outside of the room that contains the MRI machine.

The tubing connects the valves 420 to the pneumatic pistons 300, 310, 320 using an access port between the MRI machine room and the control room. Pressure can be supplied from a wall outlet.

As described previously and as set forth in FIG. 27, the foot stressor 100 involves constrained kinematics to displace the ball of the foot in the desired directions and in particular, uses a force application mechanism, which comprises the saddle 190 and the column support 160, to displace the foot.

The pneumatic piston 300, 310, 320 can have a construction that is illustrated in FIGS. 12-16. Accordingly, while the following discussion will reference the construction of the first actuator 300, it will be understood that the second actuator 310 and the third actuator 320 preferably have the same construction and therefore, the second actuator 310 and third actuator 320 include the same components described below with reference to the first actuator 300.

The pneumatic piston 300 includes a cylinder (body) 340 that has a first end 342 and an opposing second end 344. The first end 342 is an open end and similarly, the second end 344 is an open end. The cylinder 340 has a cylindrical shape. As shown, the opening at the first end 342 can be smaller than the opening at the second end 344. The openings at the first end 342 and the second end 344 can be circular shaped. The cylinder 340 also has a first side opening 346 that provides communication to the hollow interior of the cylinder 340. The first side opening 346 can also have a circular shape.

At the first end 342 of the cylinder 340 a tubular extension (a boss) 350 projects outwardly from the first end 342 and can have a cylindrical shape. The diameter of the tubular extension 350 is less than the diameter of the cylinder 340 and therefore a right angle shoulder is formed and an annular shaped landing is formed about the tubular extension 350. Within the cylinder 340 is a movable piston 360 that under an applied pneumatic force is configured to slide within the hollow interior of the cylinder 340. The piston 360 is formed of a piston rod 370 that has a first end 372 and an opposing second end 374 that comprises an end portion 375 that is enlarged relative to the elongated piston rod 370. Both the piston rod 370 and the end portion 375 can have cylindrical shapes as illustrated. The end portion 375 is configured to sealingly contact and seal the inner surface of the cylinder 340. The end portion 375 has one more O-rings 380 to promote the sealed contact between the end portion 375 and the inner surface of the cylinder 340.

At the first end 372 of the piston rod 370 there is a bushing 379. The elongated piston rod 370 is configured to pass through the hollow bushing 380 and also pass through the opening at the first end 342 as well as pass through the tubular extension 350 and exit through the distal opening of the tubular extension 350. Accordingly, when a force is applied to the piston rod 370 to cause controlled movement thereof in a distal direction, the piston rod 370 can be projected distally beyond the tubular extension 350. As described herein, the piston rod 370 is the part that contact and applied a force to the saddle 190 to cause controlled movement thereof.

The first actuator 300 also includes an end cap 380 that has a number of internal cavities and passageways formed therein for routing air to and/or from the hollow interior of the cylinder 340. The end cap 380 is configured to be sealingly mated to the second end 344 of the cylinder 340. The end cap 380 has a first end 382 and an opposing second end 384. The first end 382 is an open end that is inserted into the second end 344 of the cylinder. An outer circular shaped groove 381 can be formed in the end cap 380 at or proximate to the first end 382 for receiving a seal member, such as an O-ring. The end cap 380 has a first bore 385 that is open at the first end 382 and is closed end in that it terminates at a location within the inside of the end cap 380. The first bore 385 can be thought of as being a longitudinal bore.

The end cap 380 also has a second bore 389 formed therein. The second bore 389 is formed and is open along a side wall of the end cap 380. The second bore 389 intersects the first bore 385 at or proximate to the closed end of the first bore 385. The second bore 389 can therefore be thought of as being a transverse bore. The fluid (air) communication between the first bore 385 and the second bore 389 thus defines a first fluid (air) flow path to allow air to be introduced into the second end of the cylinder 340 or allow the air to be evacuated from the second end of the cylinder 340. The first air flow path is thus located on a first side of the end portion 375 of the piston. A second fluid (air) flow path is defined by the side opening 346 which is located on an opposite second side of the end portion 375 of the piston.

As will be readily understood by one skilled in the art and as further described herein, the piston 360 moves based on the delivery of air to one side of the piston and evacuation of air from the other side of the piston. More specifically, when fluid is delivered along the first fluid flow path, the piston 360 moves in a distal direction resulting in extension of the piston 360. Conversely, when air is delivered along the second air flow path, the piston 360 moves in a proximal direction resulting in retraction of the piston 360 within the cylinder 340.

The pneumatic piston 300 also includes a first barbed tube connector 390 that is received within the opening 346 and a second barbed tube connector 392 that is received within the second bore 389 of the end cap 380. Each of the first barbed tube connector 390 and the second barbed tube connector 392 is configured to sealingly be coupled to the cylinder 340 and the end cap 380, respectively. As such, each connector can include a threaded end portion 395 that mates with complementary threads and can include a nipple 392 over which a tube carrying the air is received. The connectors 390, 392 provide the means for delivering air into the cylinder 340 and evacuating air from the cylinder 340.

Figure 28:
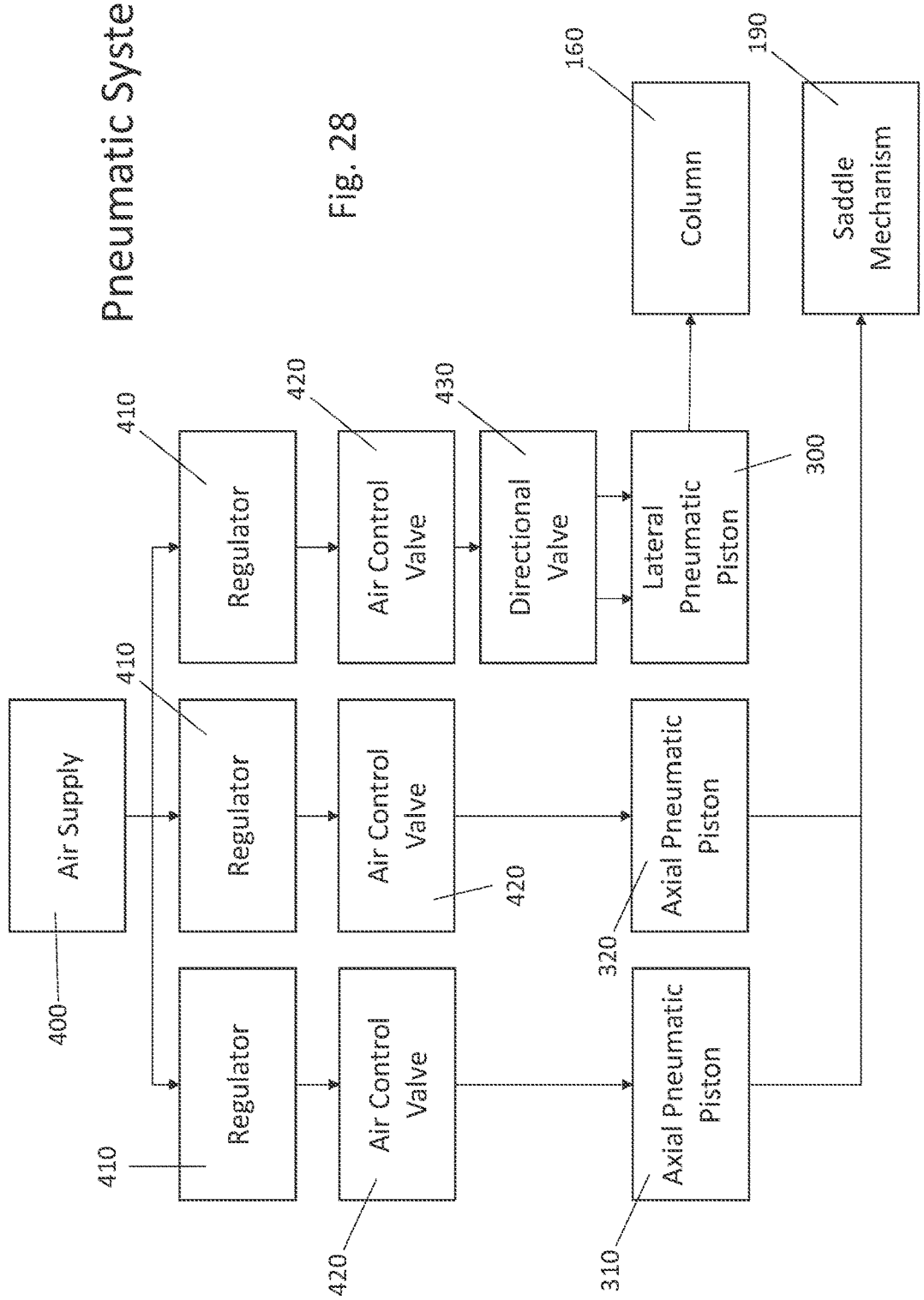
FIG. 28 is a schematic of an exemplary pneumatic system that serves as an actuator for controllably moving the force application mechanism in a plurality of different directions to apply different loads to the foot.

FIG. 28 is a schematic of an exemplary pneumatic system that includes the first pneumatic piston 300, the second pneumatic piston 310, and the third pneumatic piston 320. As discussed previously, the first actuator 300 is for moving the saddle 190 in the lateral direction. The first actuator 300 is therefore disposed within the opening 140 of the base 110 and extends along the rear face of the base 110. The distal end of the piston 370 is configured to be coupled to the protrusion 180 that is part of the column support 160 and therefore axial movement of the piston 370 is translated into axial movement of the column support 160. This axial movement of the column support 160 thus results in lateral movement of the saddle 190 that is coupled to the column support 160.

The second actuator 310 and third actuator 320 are coupled to the column support 160. As shown in FIG. 1B, the through holes formed in the end wall 162 can be hexagonally shaped that receive hex nuts for attached the cylinders 340 to the end wall 162. The piston 370 itself passes through the center holes of the hex nuts. The pistons 370 are aligned relative to the saddle 190 such that the pistons 370 can be driven into contact with an underside of the saddle 190 with the piston 370 of the second actuator 310 being closer to one end of the saddle 190, while the piston 370 of the third actuator 320 being closer to the other end of the saddle 190. In one embodiment, the distal ends of the pistons 370 of the two actuators 310, 320 are not fixedly attached to the underside of the saddle 190 and therefore, the saddle 190 is moved by a driving force of the extended piston 370. When the pistons 370 are retracted, the saddle 190 can be moved in the column support 160 in a direction toward the end wall 162. When the pistons 370 are retracted, the force applied by the foot against the saddle 190 will cause the movement of the saddle 190 in a direction toward the end wall 162. The embodiment shown in FIG. 1A operates in the same manner.

Accordingly, the pneumatic actuators 310, 320 are coupled to the column support 160 and are oriented parallel to one another in spaced relationship.

In yet another embodiment, the first actuator, second actuator and third actuator can be in the form of elongated rods (screws) that can be manually positioned relative to the saddle 190 and in particular, each of the elongated rods (screws) can be moved into contact with the saddle or can be moved in a direction away from the saddle. As the rods (screws) are manually driven into contact with the saddle 190, the saddle 190 moves in one direction, while retracting the rods (screws) allows the saddle 190 to move in the opposite direction. In this manual system, displaceable screws or rods are positioned at the same locations as the pneumatic pistons 300, 310, 320 and the forces applied to the saddle 190 and column support 160 are the same. The surgeon therefore would turn the selected screws causing the saddle 190 and/or column support 160 to be displaced and obtain feedback from the patient as to the level of discomfort that is being experienced. The screws are simply rotated in a first direction to drive the screws forward into contact with the saddle 190 and/or the column support 160 and are rotated in the opposite second direction to retract the screws away from the saddle 190 and/or the column support 160.

First Mode of Operation

Figure 19:
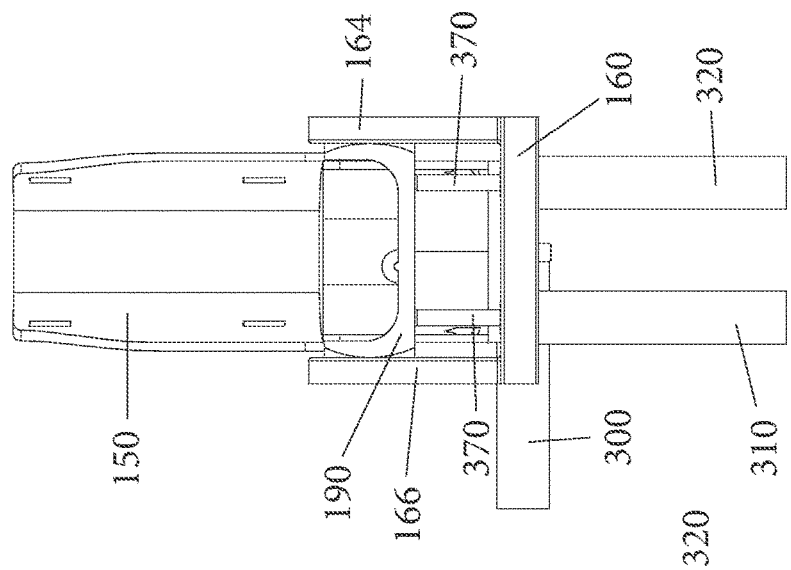
FIG. 19 is a top plan view of the assembled foot stressor.
Figure 18:
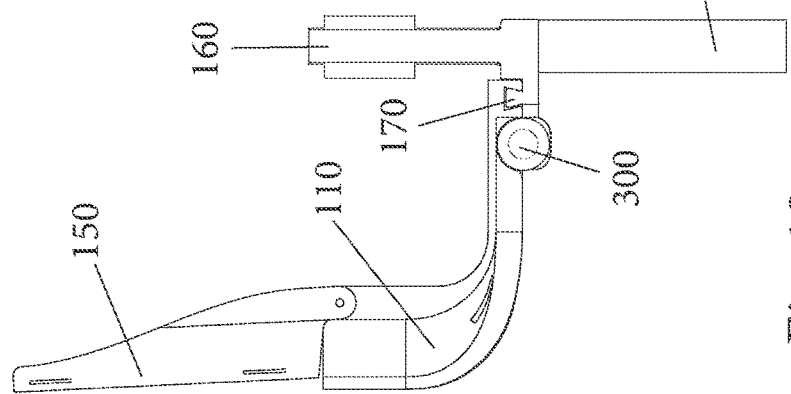
FIG. 18 is a side elevation view of the assembled foot stressor.
Figure 17:
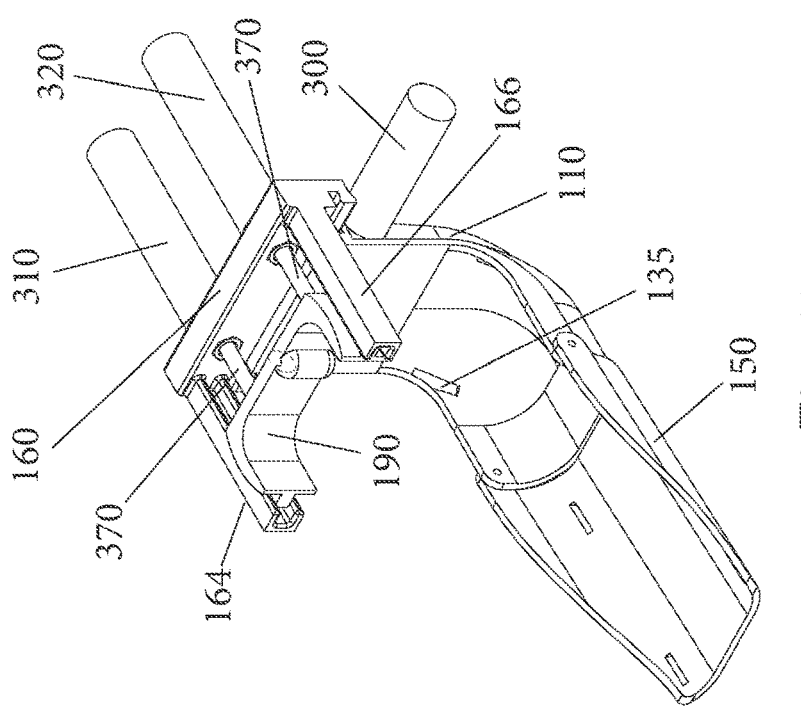
FIG. 17 is a perspective view of the foot stressor in an assembled condition and illustrating an axial load mode of operation.

FIGS. 17-19 illustrate a first mode of operation, namely, the axial displacement of the ball of the foot. Axial displacement of the foot results by actuating both of the second pneumatic actuator 310 and the third pneumatic actuator 320. By extending the pistons 370 of each of the second pneumatic actuator 310 and the third pneumatic actuator 320 at the same controlled degree of extension, the pistons 370 drive the saddle 190 within the column support 160. More specifically, the saddle 190 is driven axially (linearly) within the longitudinal tracks 165, 167 in a direction away from the end wall 162. The foot is thus placed under stress and an imaging procedure (e.g., MRI scan) is performed. As is standard practice, the recorded image is saved and identified with identifying information, such as patient name or patient ID, date, test information, such as which foot and test identifying information (e.g., which stress is being applied). Typically, the patient is loaded up to the point of discomfort. When loaded with the pistons 370, the patient can be loaded up to a predetermined maximum pressure, such as 25 psi. In one embodiment, the axial load applied is calculated based on the patient's weight. For example, the axial load can be about ¼ of the patient's weight or about ⅕ of the patient's weight or a value therebetween. As mentioned herein, one objective of the present invention is to replicate the results of the traditional physical exam in which the foot was placed under stress. Therefore, the amount of applied force can be selected to replicate the applied force that was applied during the traditional physical exam. It will also be understood that the amount of applied force that is to be applied to a foot of a given patient is dependent on a number of factors, such as the patient's age, size (weight), gender, etc.

It will be understood that the operation of the second pneumatic piston 310 and the third pneumatic piston 320 can be understood in view of the schematics of FIGS. 27 and 28 in that an operator in a control room can precisely control the amount of force being applied by controlling the degree of pressure (e.g., as by manipulation of the pressure regulator).

Second Mode of Operation

Figure 22:
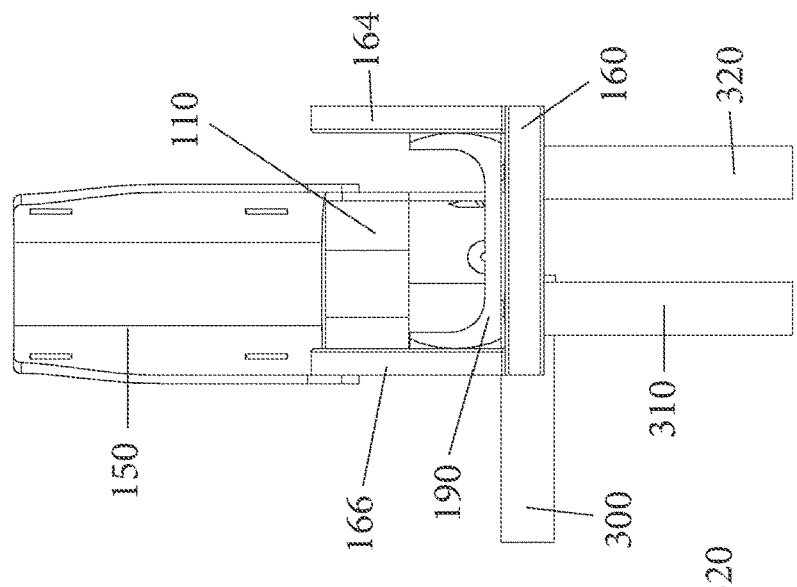
FIG. 22 is a top plan view of the assembled foot stressor.
Figure 21:
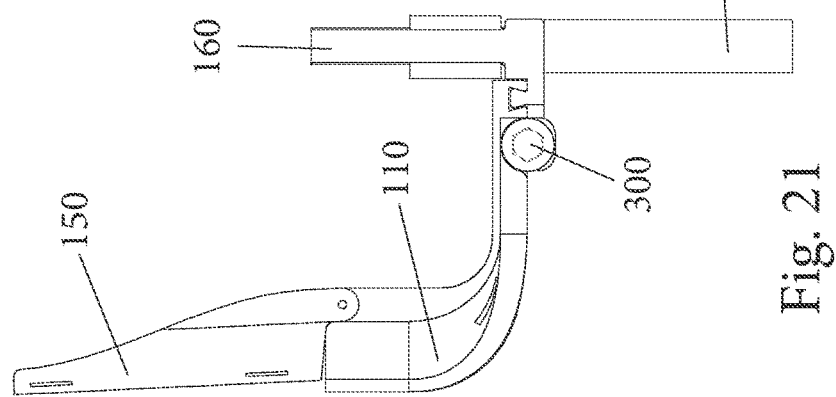
FIG. 21 is a side elevation view of the assembled foot stressor.
Figure 20:
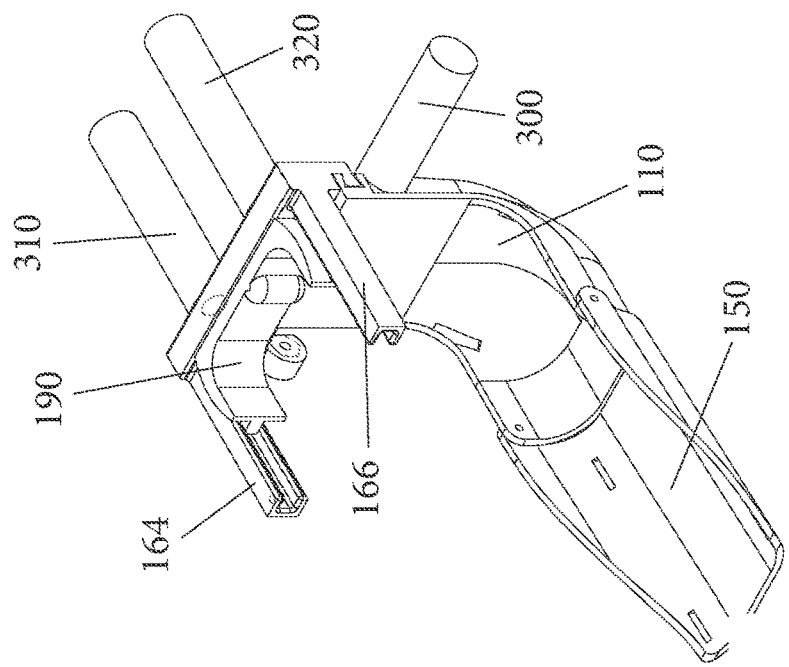
FIG. 20 is a perspective view of the foot stressor in an assembled condition and illustrating a lateral load mode of operation.

FIGS. 20-22 illustrate a second mode of operation, namely, the lateral displacement of the ball of the foot. Lateral displacement of the foot results by actuating only the first pneumatic actuator 300. By extending the piston 370 of the first pneumatic actuator 300, the piston 370 drives the column support 160 in a lateral direction (i.e., the column support 160 slides relative to the base 110). Since the saddle 190 is carried by the column support 160, the lateral movement of the column support 160 is directly translated into lateral movement of the cradle 190. As with all of the modes of operation, the foot is held in place in the base 110 by brace 150. The foot is thus placed under stress and an imaging procedure (e.g., MRI scan) is performed. As is standard practice, the recorded image is saved and identified. Typically, the patient is loaded up to the point of discomfort. When loaded with the piston 370 of the first actuator 300, the patient can be loaded up to a predetermined maximum pressure, such as 25 psi.

Third Mode of Operation

Figure 25:
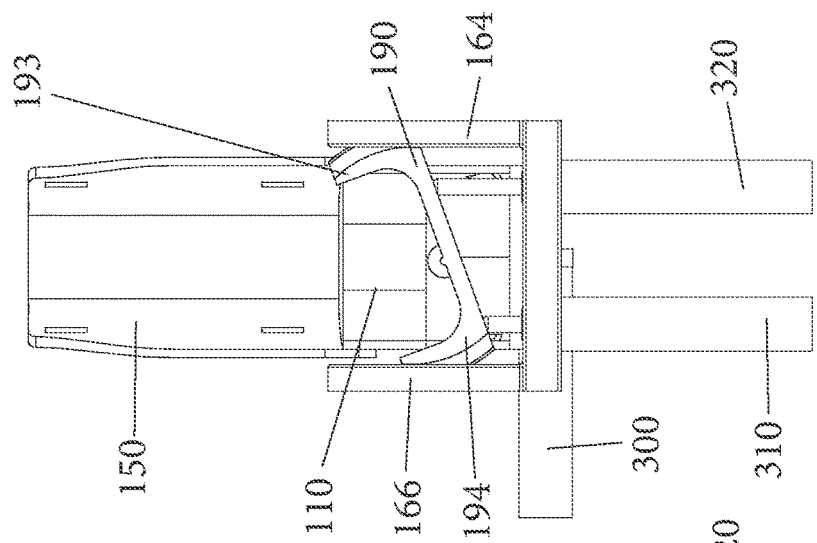
FIG. 25 is a top plan view of the assembled foot stressor.
Figure 24:
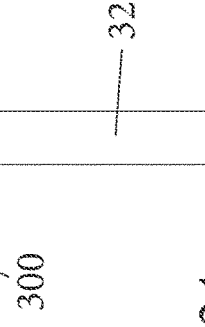
FIG. 24 is a side elevation view of the assembled foot stressor.
Figure 23:
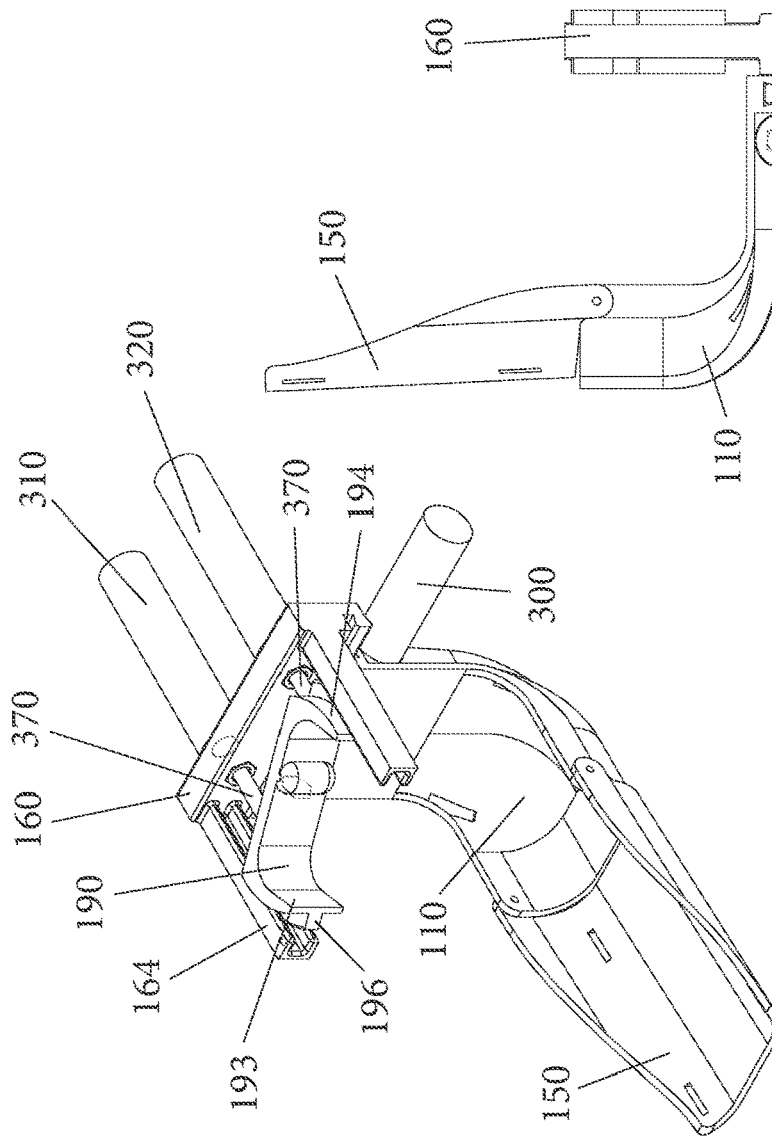
FIG. 23 is a perspective view of the foot stressor in an assembled condition and illustrating a supination load mode of operation.

FIGS. 23-25 illustrate a third mode of operation, namely, the torsional (rotational) displacement of the ball of the foot. Torsional displacement of the foot results by actuating both of the second pneumatic actuator 310 and the third pneumatic actuator 320 in opposite directions. By extending the piston 370 of only one of the second pneumatic actuator 310 and the third pneumatic actuator 320, while retracting the piston 370 of the other of the second pneumatic actuator 310 and the third pneumatic actuator 320. This actuation pattern causes the rocking of the saddle 190 within and between the columns 164, 166 as illustrated. In the embodiment shown in FIGS. 23-25, the piston 370 of the third pneumatic actuator 320 is extended, while the piston 370 of the second pneumatic actuator 310 is retracted. As mentioned previously, the curved nature of the rails 196, 197 allows the saddle 190 to rock within the longitudinal tracks 165, 167 of the column support 160. The arcuate lengths of the rails 196, 197 are selected to prevent the saddle 190 from becoming dislodged from the column support 160. In order to achieve rocking of the saddle 190 in an opposite direction, the piston 370 of the third pneumatic actuator 320 is retracted, while the piston 370 of the second pneumatic actuator 310 is extended.

The foot is thus placed under torsional stress and an imaging procedure (e.g., MRI scan) is performed. As is standard practice, the recorded image is saved and identified with identifying information. Typically, the patient is loaded up to the point of discomfort. When loaded with the pistons 370, the patient can be loaded up to a predetermined maximum pressure, such as 25 psi.

One of the advantageous features of the present device 100 is that the device is configured to apply a combination of forces (stresses) to the foot. For example, axial and torsional forces can be applied at the same time; axial and lateral forces can be applied at the same time; and lateral and torsional forces can be applied at the same time. Since all of the actuators can be easily controlled, the operator can easily select which load to apply and in some cases, as mentioned above, several different loads may be applied to the patient at the same time to observe how the foot reacts to having multiple forces applied at the same time.

The present device is thus of a dynamic nature that allows a plurality of different forces to be applied to the ball of the foot as opposed to the heel or ankle which is not desired.

Yet another advantage of the present invention is that the patient does not have to be repositioned to perform the various loading tests (axial, lateral, torsional). Instead, the patient is positioned once within the foot stressor 100 and then can be loaded into the imaging device (e.g., MRI head coil). If repositioning was required, the process would be time consuming and cumbersome.

Since one of the primary objectives of the present invention is to provide a device (foot stressor) that is compatible with imaging equipment, such as a closed, high field MRI device or CT scanners, all of the components of the present device are formed of a material that is compatible for such use. In other words, non-magnetic materials must be used. In one exemplary embodiment, the device 100 is made entirely from plastic components. In the instances in which fasteners are used, the fasteners can be in the form of nylon rivets or screws. The pneumatic pistons can be machined from polycarbonate. Straps can be made from nylon webbing with plastic buckles. Foam rubber can be used for padding.

MRI imaging to diagnose Lisfranc joint injuries (e.g., instability) offers advantages over traditional X-rays since MR images allow the surgeon to look at the state of the soft tissues of the patient. For example, the surgeon can look at tendons and ligaments as well as bone. This provides more preoperative information to the surgeon and also allows the surgeon to assess the condition of surrounding tissue (e.g., can assess whether other ligaments are injured).

The present diagnostic system also can include the use of MRI markers. The marker can be in the form of a shaped body with hollow tubes corresponding to a set of right-handed axes. These tubes are filled with a suitable fluid (e.g., mineral oil, vitamin E, water) to make them visible in the MRI images and then are detachably fixed to the device 100 as by using a fastener. For example, hook and loop fasteners can be used to attach one marker to the saddle 190 and one under the base 110. The markers were visible during the MRI tests and provides device orientation data and in particular reference points to the MR images for easier measurement.

Examples

Healthy Volunteers

Healthy control patients were put into the device 100 and loaded into an MRI machine. The device 100 was stabilized in an MRI head coil using foam, tape and inflatable pads. The MRI technician took a scout scan to select slices and choose the field of view and then took a control set of images with the foot relaxed. Then, for each loading case, the foot was stressed with the device 100, and the MRI scan process was repeated.

Images were taken for the axial test, the lateral test and the torsional test. Each of the images was checked for evidence of loading. Since the patient had healthy feet, joint instability was not expected, so more subtle evidence was sought. In addition, the observing doctors made qualitative analyses of the device 100, considering how the device works with an injured patient's foot. A control set establishes a baseline appearance of the Lisfranc joint for the patient. The results obtained indicate the bones are correctly aligned and the Lisfranc ligament was visible as a dark band from the medial cuneiform to the second metatarsal. For one patient that had a previously injured foot, the Lisfranc ligament is blurred and lighter in appearance which indicates previous damage to it.

The three axially loaded sets show evidence of the loads in the MR images. In two of the sets, sagittal images show a depression under the ball of the foot where the saddle pushes up on the foot. There was no visible differences in the actual joint between the loaded and unloaded images, as expected. In the case of the previously injured ligament, the observing surgeon noted that the very lack indicated a healthy joint despite the MRI evidence of damage. Had this been an injured patient's foot, the results would indicate that surgery was unnecessary.

The lateral test showed evidence of forcing of the heads on the metatarsals. The first metatarsal was visibly closer to the second metatarsal, rotated around its base. In the case of an injured patient, the load could result in separation rather than rotation or an even larger displacement.

The torsional test appeared to show more stretching of the ligament; however, this was more likely the result of a difference in the slice selection rather than any actual physical response.

The device 100 was fully invisible in all tests.

Injured Volunteer

A volunteer patient who had a clinical diagnosis of previous Lisfranc ligament injury was consented and put into the device 100 and loaded into an MRI machine. The device 100 was stabilized in an MRI head coil using foam, tape and inflatable pads. The MRI technician took a scout scan to select slices and choose the field of view and then took a control set of images with the foot relaxed. Then, for each loading case, the foot was stressed with the device 100, and the MRI scan process was repeated.

Images were taken for the axial test, the lateral test and the torsional test. Unloaded images demonstrated abnormal bone separation between the medial cuneiform (first cuneiform) and the base of the second metatarsal bones consistent with the patient's known diagnosis of previous Lisfranc ligament injury. Loaded images demonstrated increased separation of the bones by as much as 50%, specifically with the axial load, indicating Lisfranc joint instability. The patient reported some discomfort during the applied foot loads but tolerated well the full examination without complications. Based on the MRI results, the patient's doctor, a foot and ankle orthopedic specialist decided to perform surgery and stabilize the Lisfranc joint.

The MRI compatible foot stressor 100 is configured to reduce the uncertainty in diagnosing Lisfranc injuries. Tests on both healthy and injured volunteers indicate that the device 100 can safely and reliably apply loads to the Lisfranc joint. The device 100 was fully invisible in all tests and did not produce image artifacts. Stressed and unstressed sets of images could be taken in the time of a single appointment.

The foot stressor 100 provides a number of desirable features including but not limited to the following features. The foot stressor 100 is MRI-invisible and therefore it does not obstruct scans. The foot stressor 100 is also configured and compact enough such that it fits well inside a head coil of a closed, high field MRI device, which helps optimize the image quality. The foot stressor 100 is also configured such that it can be used in a CT scanner easily, which would be a faster process without dimensional constraints, but would not provide as much detail on soft tissues.

Moreover, the foot stressor 100 is configured to safely apply forces to the foot and therefore, there is minimal risk of further injuring the patient. A doctor can reliably control the foot stressor 100 and obtain the foot displacements that the doctor expects. The foot stressor 100 can be worn comfortably by a healthy patient for the duration of the MRI test and at most, slight soreness is experienced by the patient after the test.

As mentioned herein, one of the advantages of the present invention is the compact nature of the device 100 and in particular, the compact nature of the device 100 allows the device to be used with a number of smaller, high resolution coils. For example, the device 100 is configured and sized to fit inside extremity coils that are used in closed, high field MR machines which offer better image resolution. Other commercially available or otherwise proposed devices are not compact but rather are fairly bulky and thus, cannot be used in such smaller coils and instead can only be used in open, lower field magnets that offer lower resolution. In one embodiment, the device 100 is constructed and has a small enough footprint to be used in closed, high field magnets (1.5 or 3.0 Tesla), contained inside RF extremity coils that give higher resolution images.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A device for applying a plurality of different loads to a foot for diagnosing a foot injury of a patient comprising:
   a main body that is configured to receive and hold the foot and lower leg of the patient;
   a force application mechanism that is configured to apply a plurality of different loads to the patient's foot, wherein one or more loads can be applied to the foot at a given time; and
   a plurality of actuators for controllably moving the force application mechanism so as to apply the one or more loads to the foot;
   wherein the device is entirely made of components that are MRI compatible;
   wherein the force application mechanism comprises: (a) a support member that is coupled to the main body such that the support member can move laterally relative to the main body; and (b) a saddle that is coupled to and is configured to move both axially and rotationally relative to the support member, wherein the saddle has an inner face for receiving a ball of the foot;

wherein the plurality of actuators comprises a first axial actuator and a second axial actuator that contact and urge the saddle to move axially or rotationally depending on whether at least one of the first axial actuator and the second axial actuator is operated or both of the first axial actuator and the second axial actuator are operated at the same time;

wherein the support member has an end wall and first and second legs that extend outwardly from the end wall and are spaced from one another and are parallel to one another, the first leg defining a first longitudinal track and the second leg defining a second longitudinal track that is spaced apart and is parallel to the first longitudinal track; and the saddle is received within the first and second longitudinal tracks and is configured to move both axially and rotationally within the first and second longitudinal tracks, wherein the plurality of actuators further comprises a third actuator for applying a lateral load to a ball of the foot, the first and second axial actuators passing through spaced openings formed in the end wall of the support member to allow direct contact between the first and second axial actuators and an outer face of the saddle that is constrained within the support member, the third actuator passing along a rear face of the main body and being configured to contact and laterally drive the support member relative to the main body.

2. The device of claim 1, wherein the foot injury comprises a Lisfranc joint injury.

3. The device of claim 1, wherein the main body has three degrees of freedom.

4. The device of claim 3, wherein the main body is configured to move in an axial direction to apply an axial load to the foot, a lateral direction to apply a lateral load to the foot and a rotational (torsional) direction to apply a torsional load to the foot.

5. The device of claim 1, wherein the main body comprises a curved base that receives at least a heel portion of the foot and a brace that is coupled to the curved base for receiving a lower leg of the patient for restraining movement of the patient's ankle and heel, the force application mechanism being slidably coupled to the base for applying a lateral load to the foot.

6. The device of claim 5, wherein the brace extends to a mid-calf location of the patient.

7. The device of claim 5, further including a clamp that is detachably coupled to the curved base and is configured to cover the ankle and at least a portion of the foot.

8. The device of claim 5, wherein the clamp comprises a curved body that is split into a first half and a second half to allow for lateral clamping about the ankle and foot and at least one fastener couples the clamp to the main body by traveling over the clamp.

9. The device of claim 8, wherein the main body is defined by a pair of opposing curved side walls and the brace is defined by a pair of opposing curved side walls, wherein the main body includes a first set of openings formed therein for receiving the strap.

10. The device of claim 1, wherein the force application mechanism is slidingly coupled to the main body by a dovetail joint.

11. The device of claim 1, wherein the support member is slidingly coupled to the main body such that when a lateral force is applied thereto, the support member slides relative to the main body.

12. The device of claim 11, wherein the rear face of the main body includes a tail that extends transversely across the main body and support member includes a dovetail pin that is received within the tail along the rear face to form a dovetail joint.

13. The device of claim 1, wherein the saddle has an inner face for receiving a ball of the foot, a first curved end and an opposing second curved end, the first curved end having a first curved rail that is received within the first longitudinal track and the second curved end having a second curved rail that is received within the second longitudinal track.

14. The device of claim 1, wherein the support member includes a protrusion that extends outwardly from the end wall and is located proximate one end of the end wall.

15. The device of claim 1, wherein uniform actuation of the first and second axial actuators results in an axial load being applied to the ball of the foot.

16. The device of claim 1, wherein actuation of only one of the first and second axial actuators results in a torsional load being applied to the ball of the foot.

17. The device of claim 1, wherein the plurality of actuators are selected from the group consisting of push-pull cable, hydraulic actuators, pneumatic actuators, and manually displaceable screws.

18. The device of claim 1, wherein the third actuator comprises a first pneumatic piston, the first axial actuator comprises a second pneumatic piston, and the second axial actuator comprises a third pneumatic piston, wherein each of the first, second and third pneumatic pistons includes a cylinder in which a movable piston is contained, the movable piston having an enlarged end portion that sealingly contacts an inner wall of the cylinder and partitions the pneumatic piston into a first air compartment located distal to the enlarged end portion and a second air compartment located proximal to the enlarged end portion.

19. The device of claim 18, wherein each of the first pneumatic piston, the second pneumatic piston and the third pneumatic piston includes a first air port that communicates with the first air compartment and a second air port that communicates with the second air compartment.

20. The device of claim 19, wherein each of the first pneumatic piston, the second pneumatic piston and the third pneumatic piston includes an end cap secured to one end of the cylinder, the first air port being formed in the cylinder and the second air port being formed in the end cap.

21. The device of claim 1, wherein the third actuator, the first axial actuator and the second axial actuator are part of a pneumatic system that further includes: (a) an air source that is fluidly connected to each of the third actuator, the first axial actuator and the second axial actuator, (b) a plurality of air control valves for controlling air flow to the third actuator, the first axial actuator and the second axial actuator; and (c) a pressure regulator for regulating an amount of pressure delivered to one or more of the third actuator, the first axial actuator and the second axial actuator.

22. The device of claim 1, wherein an amount of each load is variable and selectable.

23. The device of claim 1, wherein the first axial actuator applies a first axial load to the saddle and the second axial actuator applies a second axial load to the saddle, the first and second axial loads being perpendicular to a rear of the saddle.

24. A device for applying a plurality of different loads to a foot for diagnosing a foot injury of a patient comprising:
a main body that is configured to receive and hold the foot and lower leg of the patient;

a force application mechanism that is configured to apply a plurality of different loads to the patient's foot, wherein one or more loads can be applied to the foot at a given time; and a plurality of actuators for controllably moving the force application mechanism so as to apply the one or more loads to the foot;

wherein the device is entirely made of components that are MRI compatible;

wherein the force application mechanism comprises: (a) a support member that has a base portion and first and second legs that extend outwardly from the base portion and are spaced from one another; and (b) a saddle that is received between the first and second legs and is configured to move both axially and rotationally relative to the support member, wherein the saddle has an inner face for receiving a ball of the foot;

wherein the inner face includes an off-centered bump that is formed at a location that corresponds to a second metatarsal of the foot so as to pre-stress a Lisfranc joint of the patient's foot.

25. An MRI-compatible device for applying a plurality of different loads to a foot for evaluating the Lisfranc joint of a patient comprising:

a base that is configured to receive and hold the foot and lower leg of the patient;

a force application assembly that is configured to apply the plurality of different loads to the patient's foot, wherein the force application assembly is configured such that one or more loads can be applied to the foot at a given time, the plurality of different loads including an axial load, a lateral load, and a torsional load, the force application assembly comprising a support member that is slidably coupled to the base for delivering a lateral load to a ball of the foot and a saddle that has an inner face against which the ball of the foot is placed and an opposite outer face, the saddle being coupled to and carried by the support member such that the saddle can move in an axial direction within the support member for applying an axial load to the ball of the foot and can move in a torsional direction within the support member for applying a torsional load to the foot; and a plurality of actuators for controllably moving the force application assembly relative to the base, the plurality of actuators including a first actuator for driving the support member in a lateral direction to apply the lateral load to the ball of the foot and second and third actuators that drive the saddle to allow both the axial load and the torsional load to be applied to the ball of the foot depending upon the actuation state of each of the second and third actuators, wherein the second and third actuators are oriented along axes that are perpendicular to the outer face of the saddle to allow the second and third actuators to contact the outer face of the saddle and drive the saddle forward;

wherein the device is entirely made of components that are MRI-compatible.

26. The device of claim 25, wherein the device is configured for reception into and containment within an MRI head coil for a closed 1.5 Tesla magnet.

27. The device of claim 25, wherein the plurality of actuators are selected from the group consisting of push-pull cable, hydraulic actuators, pneumatic actuators, and manually displaceable screws.

28. The device of claim 25, wherein the support member and the saddle are positioned at the ball of the foot so as to prevent the plurality of different loads from being applied to the ankle or heel of the patient.

29. The device of claim 25, wherein the support member that has a base portion and first and second legs that extend outwardly from the base portion and are spaced from one another, the first leg defining a first longitudinal track and the second leg defining a second longitudinal track; and the saddle is received within the first and second longitudinal tracks and is configured to move both axially and rotationally therein.

30. The device of claim 25, wherein a rear face of the base includes a tail that extends transversely across the base and support member includes a dovetail pin that is received within the tail along the rear face to form a dovetail joint.

31. The device of claim 29, wherein the saddle has an inner face for receiving the ball of the foot, a first curved end and an opposing second curved end, the first curved end having a first curved rail that is received within the first longitudinal track and the second curved end having a second curved rail that is received within the second longitudinal track, the curvature of the first and second curved rails permitting a degree of rotation of the saddle within the first and second longitudinal tracks of the support member.

32. A method for evaluating the Lisfranc joint of a patient using imaging equipment comprising the steps of:

inserting a foot of the patient into a device that is compatible with the imaging equipment, the device including a base that is configured to receive and hold the foot and lower leg of the patient and a force application assembly that is configured to apply an axial load, a lateral load, and a torsional load to a ball region of the patient's foot, wherein the force application assembly includes a support member and a saddle that is coupled to and moves within and relative to the support member;

inserting the device into the imaging equipment;

applying the axial load to the ball region by applying the axial load along an axis that is perpendicular to an outer face of the saddle that is opposite an inner face against which the foot rests and subsequently recording a first image;

applying the lateral load to the ball region and subsequently recording a second image;

applying the torsional load to the ball region by applying the torsional load along an axis that is perpendicular to the outer face of the saddle and subsequently recording a third image; and evaluating the first, second and third images to assess a state of the Lisfranc joint.

* * * * *